(12) United States Patent
Ahamed

(10) Patent No.: US 12,156,651 B2
(45) Date of Patent: Dec. 3, 2024

(54) SURGICAL STAPLING DEVICE

(71) Applicant: Covidien LP, Mansfield, MA (US)

(72) Inventor: Syed Sarfraz Ahamed, Shanghai (CN)

(73) Assignee: Covidien LP, Mansfield, MA (US)

(*) Notice: Subject to any disclaimer, the term of this patent is extended or adjusted under 35 U.S.C. 154(b) by 59 days.

(21) Appl. No.: 17/797,025

(22) PCT Filed: Feb. 3, 2020

(86) PCT No.: PCT/CN2020/074186
§ 371 (c)(1),
(2) Date: Aug. 2, 2022

(87) PCT Pub. No.: WO2021/155487
PCT Pub. Date: Aug. 12, 2021

(65) Prior Publication Data
US 2023/0060878 A1    Mar. 2, 2023

(51) Int. Cl.
*A61B 17/064* (2006.01)
*A61B 17/068* (2006.01)
*A61B 17/00* (2006.01)
*A61B 17/072* (2006.01)

(52) U.S. Cl.
CPC .. *A61B 17/068* (2013.01); *A61B 2017/00367* (2013.01); *A61B 2017/07271* (2013.01)

(58) Field of Classification Search
CPC .................. A61B 17/068; A61B 17/07292
See application file for complete search history.

(56) References Cited

U.S. PATENT DOCUMENTS

| | | |
|---|---|---|
| 3,499,591 A | 3/1970 | Green |
| 3,777,538 A | 12/1973 | Weatherly et al. |
| 3,882,854 A | 5/1975 | Hulka et al. |
| 4,027,510 A | 6/1977 | Hiltebrandt |
| 4,086,926 A | 5/1978 | Green et al. |
| 4,241,861 A | 12/1980 | Fleischer |
| 4,244,372 A | 1/1981 | Kapitanov et al. |

(Continued)

FOREIGN PATENT DOCUMENTS

| | | |
|---|---|---|
| AU | 198654765 | 9/1986 |
| CA | 2773414 A1 | 11/2012 |

(Continued)

OTHER PUBLICATIONS

Japanese Office Action dated Oct. 27, 2023, issued in corresponding JP Appln. No. 2022545989, 7 pages.

(Continued)

*Primary Examiner* — Eyamindae C Jallow

(57) ABSTRACT

A surgical stapling device (10) includes a drive assembly (70) and a tool assembly (16). The tool assembly (16) has a pair of jaws (29,31) supporting a cartridge assembly (32) and an anvil (30). The drive assembly (70) has a clamping member (74) that is movable through the tool assembly (16) to eject staples from the cartridge assembly (32) into the anvil (30) and to dissect tissue. The clamp member (74) includes an extension (84) that engages one of the jaws (29,31) to urge the distal end of the engaged jaw (29) in relation to the other jaw (31) to urge the tool assembly (16) towards an insertion position to minimize the diameter of the tool assembly (16) at a distal end of the tool assembly (16).

14 Claims, 8 Drawing Sheets

(56) References Cited

U.S. PATENT DOCUMENTS

| | | |
|---|---|---|
| 4,429,695 A | 2/1984 | Green |
| 4,505,414 A | 3/1985 | Filipi |
| 4,520,817 A | 6/1985 | Green |
| 4,589,413 A | 5/1986 | Malyshev et al. |
| 4,596,351 A | 6/1986 | Fedotov et al. |
| 4,602,634 A | 7/1986 | Barkley |
| 4,605,001 A | 8/1986 | Rothfuss et al. |
| 4,608,981 A | 9/1986 | Rothfuss et al. |
| 4,610,383 A | 9/1986 | Rothfuss et al. |
| 4,633,861 A | 1/1987 | Chow et al. |
| 4,633,874 A | 1/1987 | Chow et al. |
| 4,671,445 A | 6/1987 | Barker et al. |
| 4,700,703 A | 10/1987 | Resnick et al. |
| 4,703,887 A | 11/1987 | Clanton et al. |
| 4,728,020 A | 3/1988 | Green et al. |
| 4,752,024 A | 6/1988 | Green et al. |
| 4,784,137 A | 11/1988 | Kulik et al. |
| 4,863,088 A | 9/1989 | Redmond et al. |
| 4,869,415 A | 9/1989 | Fox |
| 4,892,244 A | 1/1990 | Fox et al. |
| 4,955,959 A | 9/1990 | Tompkins et al. |
| 4,978,049 A | 12/1990 | Green |
| 4,991,764 A | 2/1991 | Mericle |
| 5,014,899 A | 5/1991 | Presty et al. |
| 5,031,814 A | 7/1991 | Tompkins et al. |
| 5,040,715 A | 8/1991 | Green et al. |
| 5,065,929 A | 11/1991 | Schulze et al. |
| 5,071,430 A | 12/1991 | de Salis et al. |
| 5,074,454 A | 12/1991 | Peters |
| 5,083,695 A | 1/1992 | Foslien et al. |
| 5,084,057 A | 1/1992 | Green et al. |
| 5,106,008 A | 4/1992 | Tompkins et al. |
| 5,111,987 A | 5/1992 | Moeinzadeh et al. |
| 5,129,570 A | 7/1992 | Schulze et al. |
| 5,141,144 A | 8/1992 | Foslien et al. |
| 5,156,315 A | 10/1992 | Green et al. |
| 5,156,614 A | 10/1992 | Green et al. |
| 5,163,943 A | 11/1992 | Mohiuddin et al. |
| 5,170,925 A | 12/1992 | Madden et al. |
| 5,171,247 A | 12/1992 | Hughett et al. |
| 5,173,133 A | 12/1992 | Morin et al. |
| 5,180,092 A | 1/1993 | Crainich |
| 5,188,274 A | 2/1993 | Moeinzadeh et al. |
| 5,220,928 A | 6/1993 | Oddsen et al. |
| 5,221,036 A | 6/1993 | Takase |
| 5,242,457 A | 9/1993 | Akopov et al. |
| 5,246,156 A | 9/1993 | Rothfuss et al. |
| 5,253,793 A | 10/1993 | Green et al. |
| 5,263,629 A | 11/1993 | Trumbull et al. |
| RE34,519 E | 1/1994 | Fox et al. |
| 5,275,323 A | 1/1994 | Schulze et al. |
| 5,282,807 A | 2/1994 | Knoepfler |
| 5,289,963 A | 3/1994 | McGarry et al. |
| 5,307,976 A | 5/1994 | Olson et al. |
| 5,308,576 A | 5/1994 | Green et al. |
| 5,312,023 A | 5/1994 | Green et al. |
| 5,318,221 A | 6/1994 | Green et al. |
| 5,326,013 A | 7/1994 | Green et al. |
| 5,328,077 A | 7/1994 | Lou |
| 5,330,486 A | 7/1994 | Wilk |
| 5,332,142 A | 7/1994 | Robinson et al. |
| 5,336,232 A | 8/1994 | Green et al. |
| 5,344,061 A | 9/1994 | Crainich |
| 5,352,238 A | 10/1994 | Green et al. |
| 5,356,064 A | 10/1994 | Green et al. |
| 5,358,506 A | 10/1994 | Green et al. |
| 5,364,001 A | 11/1994 | Bryan |
| 5,364,002 A | 11/1994 | Green et al. |
| 5,364,003 A | 11/1994 | Williamson, IV |
| 5,366,133 A | 11/1994 | Geiste |
| 5,376,095 A | 12/1994 | Ortiz |
| 5,379,933 A | 1/1995 | Green et al. |
| 5,381,943 A | 1/1995 | Allen et al. |
| 5,382,255 A | 1/1995 | Castro et al. |
| 5,383,880 A | 1/1995 | Hooven |
| 5,389,098 A | 2/1995 | Tsuruta et al. |
| 5,395,033 A | 3/1995 | Byrne et al. |
| 5,395,034 A | 3/1995 | Allen et al. |
| 5,397,046 A | 3/1995 | Savage et al. |
| 5,397,324 A | 3/1995 | Carroll et al. |
| 5,403,312 A | 4/1995 | Yates et al. |
| 5,405,072 A | 4/1995 | Zlock et al. |
| 5,407,293 A | 4/1995 | Crainich |
| 5,413,268 A | 5/1995 | Green et al. |
| 5,415,334 A | 5/1995 | Williamson et al. |
| 5,415,335 A | 5/1995 | Knodell, Jr. |
| 5,417,361 A | 5/1995 | Williamson, IV |
| 5,423,471 A | 6/1995 | Mastri et al. |
| 5,425,745 A | 6/1995 | Green et al. |
| 5,431,322 A | 7/1995 | Green et al. |
| 5,431,323 A | 7/1995 | Smith et al. |
| 5,433,721 A | 7/1995 | Hooven et al. |
| 5,441,193 A | 8/1995 | Gravener |
| 5,445,304 A | 8/1995 | Plyley et al. |
| 5,447,265 A | 9/1995 | Vidal et al. |
| 5,452,837 A | 9/1995 | Williamson, IV et al. |
| 5,456,401 A | 10/1995 | Green et al. |
| 5,464,300 A | 11/1995 | Crainich |
| 5,465,895 A | 11/1995 | Knodel et al. |
| 5,467,911 A | 11/1995 | Tsuruta et al. |
| 5,470,007 A | 11/1995 | Plyley et al. |
| 5,470,010 A | 11/1995 | Rothfuss et al. |
| 5,472,132 A | 12/1995 | Savage et al. |
| 5,474,566 A | 12/1995 | Alesi et al. |
| 5,476,206 A | 12/1995 | Green et al. |
| 5,478,003 A | 12/1995 | Green et al. |
| 5,480,089 A | 1/1996 | Blewett |
| 5,482,197 A | 1/1996 | Green et al. |
| 5,484,095 A | 1/1996 | Green et al. |
| 5,484,451 A | 1/1996 | Akopov et al. |
| 5,485,947 A | 1/1996 | Olson et al. |
| 5,485,952 A | 1/1996 | Fontayne |
| 5,486,185 A | 1/1996 | Freitas et al. |
| 5,487,499 A | 1/1996 | Sorrentino et al. |
| 5,487,500 A | 1/1996 | Knodel et al. |
| 5,489,058 A | 2/1996 | Plyley et al. |
| 5,490,856 A | 2/1996 | Person et al. |
| 5,497,933 A | 3/1996 | DeFonzo et al. |
| 5,501,689 A | 3/1996 | Green et al. |
| 5,505,363 A | 4/1996 | Green et al. |
| 5,507,426 A | 4/1996 | Young et al. |
| 5,518,163 A | 5/1996 | Hooven |
| 5,518,164 A | 5/1996 | Hooven |
| 5,529,235 A | 6/1996 | Boiarski et al. |
| 5,531,744 A | 7/1996 | Nardella et al. |
| 5,535,934 A | 7/1996 | Boiarski et al. |
| 5,535,935 A | 7/1996 | Vidal et al. |
| 5,535,937 A | 7/1996 | Boiarski et al. |
| 5,540,375 A | 7/1996 | Bolanos et al. |
| 5,542,594 A | 8/1996 | McKean et al. |
| 5,549,628 A | 8/1996 | Cooper et al. |
| 5,551,622 A | 9/1996 | Yoon |
| 5,553,765 A | 9/1996 | Knodel et al. |
| 5,554,164 A | 9/1996 | Wilson et al. |
| 5,554,169 A | 9/1996 | Green et al. |
| 5,560,530 A | 10/1996 | Bolanos et al. |
| 5,560,532 A | 10/1996 | DeFonzo et al. |
| 5,562,239 A | 10/1996 | Boiarski et al. |
| 5,562,241 A | 10/1996 | Knodel et al. |
| 5,562,682 A | 10/1996 | Oberlin et al. |
| 5,562,701 A | 10/1996 | Huitema et al. |
| 5,564,615 A | 10/1996 | Bishop et al. |
| 5,571,116 A | 11/1996 | Bolanos et al. |
| 5,573,169 A | 11/1996 | Green et al. |
| 5,573,543 A | 11/1996 | Akopov et al. |
| 5,575,799 A | 11/1996 | Bolanos et al. |
| 5,575,803 A | 11/1996 | Cooper et al. |
| 5,577,654 A | 11/1996 | Bishop |
| 5,584,425 A | 12/1996 | Savage et al. |
| 5,586,711 A | 12/1996 | Plyley et al. |
| 5,588,580 A | 12/1996 | Paul et al. |
| 5,588,581 A | 12/1996 | Conlon et al. |
| 5,597,107 A | 1/1997 | Knodel et al. |
| 5,601,224 A | 2/1997 | Bishop et al. |

(56) References Cited

U.S. PATENT DOCUMENTS

| | | |
|---|---|---|
| 5,607,095 A | 3/1997 | Smith et al. |
| 5,615,820 A | 4/1997 | Viola |
| 5,618,291 A | 4/1997 | Thompson et al. |
| 5,624,452 A | 4/1997 | Yates |
| 5,626,587 A | 5/1997 | Bishop et al. |
| 5,628,446 A | 5/1997 | Geiste et al. |
| 5,630,539 A | 5/1997 | Plyley et al. |
| 5,630,540 A | 5/1997 | Blewett |
| 5,630,541 A | 5/1997 | Williamson, IV et al. |
| 5,632,432 A | 5/1997 | Schulze et al. |
| 5,634,584 A | 6/1997 | Okorocha et al. |
| 5,636,780 A | 6/1997 | Green et al. |
| 5,645,209 A | 7/1997 | Green et al. |
| 5,647,526 A | 7/1997 | Green et al. |
| 5,651,491 A | 7/1997 | Heaton et al. |
| 5,653,373 A | 8/1997 | Green et al. |
| 5,653,374 A | 8/1997 | Young et al. |
| 5,653,721 A | 8/1997 | Knodel et al. |
| 5,655,698 A | 8/1997 | Yoon |
| 5,657,921 A | 8/1997 | Young et al. |
| 5,658,300 A | 8/1997 | Bito et al. |
| 5,662,258 A | 9/1997 | Knodel et al. |
| 5,662,259 A | 9/1997 | Yoon |
| 5,662,260 A | 9/1997 | Yoon |
| 5,662,662 A | 9/1997 | Bishop et al. |
| 5,662,666 A | 9/1997 | Onuki et al. |
| 5,665,085 A | 9/1997 | Nardella |
| 5,667,517 A | 9/1997 | Hooven |
| 5,669,544 A | 9/1997 | Schulze et al. |
| 5,673,840 A | 10/1997 | Schulze et al. |
| 5,673,841 A | 10/1997 | Schulze et al. |
| 5,673,842 A | 10/1997 | Bittner et al. |
| 5,676,674 A | 10/1997 | Bolanos et al. |
| 5,680,981 A | 10/1997 | Mililli et al. |
| 5,680,982 A | 10/1997 | Schulze et al. |
| 5,680,983 A | 10/1997 | Plyley et al. |
| 5,690,269 A | 11/1997 | Bolanos et al. |
| 5,690,675 A | 11/1997 | Sawyer et al. |
| 5,692,668 A | 12/1997 | Schulze et al. |
| 5,697,542 A | 12/1997 | Knodel et al. |
| 5,702,409 A | 12/1997 | Rayburn et al. |
| 5,704,534 A | 1/1998 | Huitema et al. |
| 5,706,997 A | 1/1998 | Green et al. |
| 5,709,334 A | 1/1998 | Sorrentino et al. |
| 5,711,472 A | 1/1998 | Bryan |
| 5,713,505 A | 2/1998 | Huitema |
| 5,715,988 A | 2/1998 | Palmer |
| 5,716,366 A | 2/1998 | Yates |
| 5,718,359 A | 2/1998 | Palmer et al. |
| 5,725,536 A | 3/1998 | Oberlin et al. |
| 5,725,554 A | 3/1998 | Simon et al. |
| 5,728,110 A | 3/1998 | Vidal et al. |
| 5,732,806 A | 3/1998 | Foshee et al. |
| 5,735,848 A | 4/1998 | Yates et al. |
| 5,743,456 A | 4/1998 | Jones et al. |
| 5,749,893 A | 5/1998 | Vidal et al. |
| 5,752,644 A | 5/1998 | Bolanos et al. |
| 5,762,255 A | 6/1998 | Chrisman et al. |
| 5,762,256 A | 6/1998 | Mastri et al. |
| 5,769,303 A | 6/1998 | Knodel et al. |
| 5,769,892 A | 6/1998 | Kingwell |
| 5,772,099 A | 6/1998 | Gravener |
| 5,772,673 A | 6/1998 | Cuny et al. |
| 5,779,130 A | 7/1998 | Alesi et al. |
| 5,779,131 A | 7/1998 | Knodel et al. |
| 5,779,132 A | 7/1998 | Knodel et al. |
| 5,782,396 A | 7/1998 | Mastri et al. |
| 5,782,397 A | 7/1998 | Koukline |
| 5,782,834 A | 7/1998 | Lucey et al. |
| 5,785,232 A | 7/1998 | Vidal et al. |
| 5,797,536 A | 8/1998 | Smith et al. |
| 5,797,537 A | 8/1998 | Oberlin et al. |
| 5,797,538 A | 8/1998 | Heaton et al. |
| 5,810,811 A | 9/1998 | Yates et al. |
| 5,810,855 A | 9/1998 | Rayburn et al. |
| 5,814,055 A | 9/1998 | Knodel et al. |
| 5,814,057 A | 9/1998 | Oi et al. |
| 5,816,471 A | 10/1998 | Plyley et al. |
| 5,817,109 A | 10/1998 | McGarry et al. |
| 5,820,009 A | 10/1998 | Melling et al. |
| 5,823,066 A | 10/1998 | Huitema et al. |
| 5,826,776 A | 10/1998 | Schulze et al. |
| 5,829,662 A | 11/1998 | Allen et al. |
| 5,833,695 A | 11/1998 | Yoon |
| 5,836,147 A | 11/1998 | Schnipke |
| 5,862,972 A | 1/1999 | Green et al. |
| 5,865,361 A | 2/1999 | Milliman et al. |
| 5,871,135 A | 2/1999 | Williamson, IV et al. |
| 5,873,873 A | 2/1999 | Smith et al. |
| 5,878,938 A | 3/1999 | Bittner et al. |
| 5,893,506 A | 4/1999 | Powell |
| 5,894,979 A | 4/1999 | Powell |
| 5,897,562 A | 4/1999 | Bolanos et al. |
| 5,901,895 A | 5/1999 | Heaton et al. |
| 5,911,352 A | 6/1999 | Racenet et al. |
| 5,911,353 A | 6/1999 | Bolanos et al. |
| 5,918,791 A | 7/1999 | Sorrentino et al. |
| 5,919,198 A | 7/1999 | Graves, Jr. et al. |
| 5,922,001 A | 7/1999 | Yoon |
| 5,931,847 A | 8/1999 | Bittner et al. |
| 5,941,442 A | 8/1999 | Geiste et al. |
| 5,954,259 A | 9/1999 | Viola et al. |
| 5,964,774 A | 10/1999 | McKean et al. |
| 5,980,510 A | 11/1999 | Tsonton et al. |
| 5,988,479 A | 11/1999 | Palmer |
| 6,004,335 A | 12/1999 | Vaitekunas et al. |
| 6,010,054 A | 1/2000 | Johnson et al. |
| 6,032,849 A | 3/2000 | Mastri et al. |
| 6,045,560 A | 4/2000 | McKean et al. |
| 6,063,097 A | 5/2000 | Oi et al. |
| 6,079,606 A | 6/2000 | Milliman et al. |
| 6,099,551 A | 8/2000 | Gabbay |
| 6,109,500 A | 8/2000 | Alli et al. |
| 6,131,789 A | 10/2000 | Schulze et al. |
| 6,131,790 A | 10/2000 | Piraka |
| 6,155,473 A | 12/2000 | Tompkins et al. |
| 6,197,017 B1 | 3/2001 | Brock et al. |
| 6,202,914 B1 | 3/2001 | Geiste et al. |
| 6,241,139 B1 | 6/2001 | Milliman et al. |
| 6,250,532 B1 | 6/2001 | Green et al. |
| 6,264,086 B1 | 7/2001 | McGuckin, Jr. |
| 6,264,087 B1 | 7/2001 | Whitman |
| 6,279,809 B1 | 8/2001 | Nicolo |
| 6,315,183 B1 | 11/2001 | Piraka |
| 6,315,184 B1 | 11/2001 | Whitman |
| 6,325,810 B1 | 12/2001 | Hamilton et al. |
| 6,330,965 B1 | 12/2001 | Milliman et al. |
| 6,391,038 B2 | 5/2002 | Vargas et al. |
| 6,398,797 B2 | 6/2002 | Bombard et al. |
| 6,436,097 B1 | 8/2002 | Nardella |
| 6,439,446 B1 | 8/2002 | Perry et al. |
| 6,443,973 B1 | 9/2002 | Whitman |
| 6,478,804 B2 | 11/2002 | Vargas et al. |
| 6,488,196 B1 | 12/2002 | Fenton, Jr. |
| 6,503,257 B2 | 1/2003 | Grant et al. |
| 6,505,768 B2 | 1/2003 | Whitman |
| 6,544,274 B2 | 4/2003 | Danitz et al. |
| 6,554,844 B2 | 4/2003 | Lee et al. |
| 6,565,554 B1 | 5/2003 | Niemeyer |
| 6,587,750 B2 | 7/2003 | Gerbi et al. |
| 6,592,597 B2 | 7/2003 | Grant et al. |
| 6,594,552 B1 | 7/2003 | Nowlin et al. |
| 6,602,252 B2 | 8/2003 | Mollenauer |
| 6,619,529 B2 | 9/2003 | Green et al. |
| D480,808 S | 10/2003 | Wells et al. |
| 6,644,532 B2 | 11/2003 | Green et al. |
| 6,656,193 B2 | 12/2003 | Grant et al. |
| 6,669,073 B2 | 12/2003 | Milliman et al. |
| 6,681,978 B2 | 1/2004 | Geiste et al. |
| 6,698,643 B2 | 3/2004 | Whitman |
| 6,716,232 B1 | 4/2004 | Vidal et al. |
| 6,722,552 B2 | 4/2004 | Fenton, Jr. |
| 6,755,338 B2 | 6/2004 | Hahnen et al. |
| 6,783,524 B2 | 8/2004 | Anderson et al. |

(56) References Cited

U.S. PATENT DOCUMENTS

| | | |
|---|---|---|
| 6,786,382 B1 | 9/2004 | Hoffman |
| 6,817,509 B2 | 11/2004 | Geiste et al. |
| 6,830,174 B2 | 12/2004 | Hillstead et al. |
| 6,835,199 B2 | 12/2004 | McGuckin, Jr. et al. |
| 6,843,403 B2 | 1/2005 | Whitman |
| RE38,708 E | 3/2005 | Bolanos et al. |
| 6,877,647 B2 | 4/2005 | Green et al. |
| 6,889,116 B2 | 5/2005 | Jinno |
| 6,905,057 B2 | 6/2005 | Swayze et al. |
| 6,945,444 B2 | 9/2005 | Gresham et al. |
| 6,953,138 B1 | 10/2005 | Dworak et al. |
| 6,953,139 B2 | 10/2005 | Milliman et al. |
| 6,959,852 B2 | 11/2005 | Shelton, IV et al. |
| 6,962,594 B1 | 11/2005 | Thevenet |
| 6,964,363 B2 | 11/2005 | Wales et al. |
| 6,978,921 B2 | 12/2005 | Shelton, IV et al. |
| 6,981,628 B2 | 1/2006 | Wales |
| 6,986,451 B1 | 1/2006 | Mastri et al. |
| 6,988,649 B2 | 1/2006 | Shelton, IV et al. |
| 6,991,627 B2 | 1/2006 | Madhani et al. |
| 6,994,714 B2 | 2/2006 | Vargas et al. |
| 7,000,818 B2 | 2/2006 | Shelton, IV et al. |
| 7,000,819 B2 | 2/2006 | Swayze et al. |
| 7,032,799 B2 | 4/2006 | Viola et al. |
| 7,044,352 B2 | 5/2006 | Shelton, IV et al. |
| 7,044,353 B2 | 5/2006 | Mastri et al. |
| 7,055,730 B2 | 6/2006 | Ehrenfels et al. |
| 7,055,731 B2 | 6/2006 | Shelton, IV et al. |
| 7,059,508 B2 | 6/2006 | Shelton, IV et al. |
| 7,070,083 B2 | 7/2006 | Jankowski |
| 7,083,075 B2 | 8/2006 | Swayze et al. |
| 7,097,089 B2 | 8/2006 | Marczyk |
| 7,111,769 B2 | 9/2006 | Wales et al. |
| 7,114,642 B2 | 10/2006 | Whitman |
| 7,121,446 B2 | 10/2006 | Arad et al. |
| 7,128,253 B2 | 10/2006 | Mastri et al. |
| 7,128,254 B2 | 10/2006 | Shelton, IV et al. |
| 7,140,527 B2 | 11/2006 | Ehrenfels et al. |
| 7,140,528 B2 | 11/2006 | Shelton, IV |
| 7,143,923 B2 | 12/2006 | Shelton, IV et al. |
| 7,143,924 B2 | 12/2006 | Scirica et al. |
| 7,143,925 B2 | 12/2006 | Shelton, IV et al. |
| 7,143,926 B2 | 12/2006 | Shelton, IV et al. |
| 7,147,138 B2 | 12/2006 | Shelton, IV |
| 7,159,750 B2 | 1/2007 | Racenet et al. |
| 7,168,604 B2 | 1/2007 | Milliman et al. |
| 7,172,104 B2 | 2/2007 | Scirica et al. |
| 7,188,758 B2 | 3/2007 | Viola et al. |
| 7,207,471 B2 | 4/2007 | Heinrich et al. |
| 7,213,736 B2 | 5/2007 | Nales et al. |
| 7,225,963 B2 | 6/2007 | Scirica |
| 7,225,964 B2 | 6/2007 | Mastri et al. |
| 7,238,195 B2 | 7/2007 | Viola |
| 7,246,734 B2 | 7/2007 | Shelton, IV |
| 7,258,262 B2 | 8/2007 | Mastri et al. |
| 7,267,682 B1 | 9/2007 | Bender et al. |
| 7,278,562 B2 | 10/2007 | Mastri et al. |
| 7,278,563 B1 | 10/2007 | Green |
| 7,287,682 B1 | 10/2007 | Ezzat et al. |
| 7,293,685 B2 | 11/2007 | Ehrenfels et al. |
| 7,296,722 B2 | 11/2007 | Ivanko |
| 7,296,724 B2 | 11/2007 | Green et al. |
| 7,296,772 B2 | 11/2007 | Wang |
| 7,300,444 B1 | 11/2007 | Nielsen et al. |
| 7,303,107 B2 | 12/2007 | Milliman et al. |
| 7,303,108 B2 | 12/2007 | Shelton, IV |
| 7,308,998 B2 | 12/2007 | Mastri et al. |
| 7,326,232 B2 | 2/2008 | Viola et al. |
| 7,328,828 B2 | 2/2008 | Ortiz et al. |
| 7,328,829 B2 | 2/2008 | Arad et al. |
| 7,334,717 B2 | 2/2008 | Rethy et al. |
| 7,354,447 B2 | 4/2008 | Shelton, IV et al. |
| 7,357,287 B2 | 4/2008 | Shelton, IV et al. |
| 7,364,061 B2 | 4/2008 | Swayze et al. |
| 7,367,485 B2 | 5/2008 | Shelton, IV et al. |
| 7,377,928 B2 | 5/2008 | Zubik et al. |
| 7,380,695 B2 | 6/2008 | Doll et al. |
| 7,380,696 B2 | 6/2008 | Shelton, IV et al. |
| 7,396,356 B2 | 7/2008 | Mollenauer |
| 7,398,907 B2 | 7/2008 | Racenet et al. |
| 7,399,310 B2 | 7/2008 | Edoga et al. |
| 7,401,720 B1 | 7/2008 | Durrani |
| 7,401,721 B2 | 7/2008 | Holsten et al. |
| 7,404,508 B2 | 7/2008 | Smith et al. |
| 7,404,509 B2 | 7/2008 | Ortiz et al. |
| 7,407,074 B2 | 8/2008 | Ortiz et al. |
| 7,407,075 B2 | 8/2008 | Holsten et al. |
| 7,407,077 B2 | 8/2008 | Ortiz et al. |
| 7,407,078 B2 | 8/2008 | Shelton, IV et al. |
| 7,416,101 B2 | 8/2008 | Shelton, IV et al. |
| 7,419,080 B2 | 9/2008 | Smith et al. |
| 7,419,081 B2 | 9/2008 | Ehrenfels et al. |
| 7,419,495 B2 | 9/2008 | Menn et al. |
| 7,422,139 B2 | 9/2008 | Shelton, IV et al. |
| 7,424,965 B2 | 9/2008 | Racenet et al. |
| 7,431,189 B2 | 10/2008 | Shelton, IV et al. |
| 7,431,730 B2 | 10/2008 | Viola |
| 7,434,715 B2 | 10/2008 | Shelton, IV et al. |
| 7,434,717 B2 | 10/2008 | Shelton, IV et al. |
| 7,438,208 B2 | 10/2008 | Larson |
| 7,438,209 B1 | 10/2008 | Hess et al. |
| 7,441,684 B2 | 10/2008 | Shelton, IV et al. |
| 7,441,685 B1 | 10/2008 | Boudreaux |
| 7,448,525 B2 | 11/2008 | Shelton, IV et al. |
| 7,451,904 B2 | 11/2008 | Shelton, IV |
| 7,455,208 B2 | 11/2008 | Wales et al. |
| 7,455,676 B2 | 11/2008 | Holsten et al. |
| 7,458,494 B2 | 12/2008 | Matsutani et al. |
| 7,461,767 B2 | 12/2008 | Viola et al. |
| 7,462,185 B1 | 12/2008 | Knodel |
| 7,464,846 B2 | 12/2008 | Shelton, IV et al. |
| 7,464,847 B2 | 12/2008 | Viola et al. |
| 7,464,848 B2 | 12/2008 | Green et al. |
| 7,464,849 B2 | 12/2008 | Shelton, IV et al. |
| 7,467,740 B2 | 12/2008 | Shelton, IV et al. |
| 7,472,814 B2 | 1/2009 | Mastri et al. |
| 7,472,815 B2 | 1/2009 | Shelton, IV et al. |
| 7,472,816 B2 | 1/2009 | Holsten et al. |
| 7,473,258 B2 | 1/2009 | Clauson et al. |
| 7,481,347 B2 | 1/2009 | Roy |
| 7,481,348 B2 | 1/2009 | Marczyk |
| 7,481,349 B2 | 1/2009 | Holsten et al. |
| 7,481,824 B2 | 1/2009 | Boudreaux et al. |
| 7,487,899 B2 | 2/2009 | Shelton, IV et al. |
| 7,490,749 B2 | 2/2009 | Schall et al. |
| 7,494,039 B2 | 2/2009 | Racenet et al. |
| 7,500,979 B2 | 3/2009 | Hueil et al. |
| 7,503,474 B2 | 3/2009 | Hillstead et al. |
| 7,506,790 B2 | 3/2009 | Shelton, IV |
| 7,506,791 B2 | 3/2009 | Omaits et al. |
| 7,510,107 B2 | 3/2009 | Timm et al. |
| 7,513,408 B2 | 4/2009 | Shelton, IV et al. |
| 7,517,356 B2 | 4/2009 | Heinrich |
| 7,537,602 B2 | 5/2009 | Whitman |
| 7,543,729 B2 | 6/2009 | Ivanko |
| 7,543,730 B1 | 6/2009 | Marczyk |
| 7,543,731 B2 | 6/2009 | Green et al. |
| 7,552,854 B2 | 6/2009 | Wixey et al. |
| 7,556,185 B2 | 7/2009 | Viola |
| 7,556,186 B2 | 7/2009 | Milliman |
| 7,559,450 B2 | 7/2009 | Wales et al. |
| 7,559,452 B2 | 7/2009 | Wales et al. |
| 7,559,453 B2 | 7/2009 | Heinrich et al. |
| 7,559,937 B2 | 7/2009 | de la Torre et al. |
| 7,565,993 B2 | 7/2009 | Milliman et al. |
| 7,568,603 B2 | 8/2009 | Shelton, IV et al. |
| 7,568,604 B2 | 8/2009 | Ehrenfels et al. |
| 7,571,845 B2 | 8/2009 | Viola |
| 7,575,144 B2 | 8/2009 | Ortiz et al. |
| 7,584,880 B2 | 9/2009 | Racenet et al. |
| 7,588,174 B2 | 9/2009 | Holsten et al. |
| 7,588,175 B2 | 9/2009 | Timm et al. |
| 7,588,176 B2 | 9/2009 | Timm et al. |
| 7,588,177 B2 | 9/2009 | Racenet |

(56) References Cited

U.S. PATENT DOCUMENTS

| | | |
|---|---|---|
| 7,597,229 B2 | 10/2009 | Boudreaux et al. |
| 7,597,230 B2 | 10/2009 | Racenet et al. |
| 7,600,663 B2 | 10/2009 | Green |
| 7,604,150 B2 | 10/2009 | Boudreaux |
| 7,604,151 B2 | 10/2009 | Hess et al. |
| 7,607,557 B2 | 10/2009 | Shelton, IV et al. |
| 7,611,038 B2 | 11/2009 | Racenet et al. |
| 7,617,961 B2 | 11/2009 | Viola |
| 7,624,902 B2 | 12/2009 | Marczyk et al. |
| 7,624,903 B2 | 12/2009 | Green et al. |
| 7,631,793 B2 | 12/2009 | Rethy et al. |
| 7,631,794 B2 | 12/2009 | Rethy et al. |
| 7,635,073 B2 | 12/2009 | Heinrich |
| 7,635,074 B2 | 12/2009 | Olson et al. |
| 7,635,373 B2 | 12/2009 | Ortiz |
| 7,637,409 B2 | 12/2009 | Marczyk |
| 7,637,410 B2 | 12/2009 | Marczyk |
| 7,641,091 B2 | 1/2010 | Olson et al. |
| 7,641,095 B2 | 1/2010 | Viola |
| 7,644,848 B2 | 1/2010 | Swayze et al. |
| 7,648,055 B2 | 1/2010 | Marczyk |
| 7,651,017 B2 | 1/2010 | Ortiz et al. |
| 7,654,431 B2 | 2/2010 | Hueil et al. |
| 7,658,311 B2 | 2/2010 | Boudreaux |
| 7,658,312 B2 | 2/2010 | Vidal et al. |
| 7,665,646 B2 | 2/2010 | Prommersberger |
| 7,665,647 B2 | 2/2010 | Shelton, IV et al. |
| 7,669,746 B2 | 3/2010 | Shelton, IV |
| 7,670,334 B2 | 3/2010 | Hueil et al. |
| 7,673,780 B2 | 3/2010 | Shelton, IV et al. |
| 7,673,781 B2 | 3/2010 | Swayze et al. |
| 7,673,782 B2 | 3/2010 | Hess et al. |
| 7,673,783 B2 | 3/2010 | Morgan et al. |
| 7,678,121 B1 | 3/2010 | Knodel |
| 7,681,772 B2 | 3/2010 | Green et al. |
| 7,682,367 B2 | 3/2010 | Shah et al. |
| 7,682,368 B1 | 3/2010 | Bombard et al. |
| 7,690,547 B2 | 4/2010 | Racenet et al. |
| 7,694,865 B2 | 4/2010 | Scirica |
| 7,699,205 B2 | 4/2010 | Ivanko |
| 7,703,653 B2 | 4/2010 | Shah et al. |
| 7,721,931 B2 | 5/2010 | Shelton, IV et al. |
| 7,721,933 B2 | 5/2010 | Ehrenfels et al. |
| 7,721,935 B2 | 5/2010 | Racenet et al. |
| 7,726,537 B2 | 6/2010 | Olson et al. |
| 7,726,538 B2 | 6/2010 | Holsten et al. |
| 7,726,539 B2 | 6/2010 | Holsten et al. |
| 7,731,072 B2 | 6/2010 | Timm et al. |
| 7,735,703 B2 | 6/2010 | Morgan et al. |
| 7,740,159 B2 | 6/2010 | Shelton, IV et al. |
| 7,740,160 B2 | 6/2010 | Viola |
| 7,743,960 B2 | 6/2010 | Whitman et al. |
| 7,744,628 B2 | 6/2010 | Viola |
| 7,753,245 B2 | 7/2010 | Boudreaux et al. |
| 7,753,248 B2 | 7/2010 | Viola |
| 7,757,924 B2 | 7/2010 | Gerbi et al. |
| 7,757,925 B2 | 7/2010 | Viola et al. |
| 7,762,445 B2 | 7/2010 | Heinrich et al. |
| 7,766,209 B2 | 8/2010 | Baxter, III et al. |
| 7,766,210 B2 | 8/2010 | Shelton, IV et al. |
| 7,766,924 B1 | 8/2010 | Bombard et al. |
| 7,766,928 B2 | 8/2010 | Ezzat et al. |
| 7,770,774 B2 | 8/2010 | Mastri et al. |
| 7,770,775 B2 | 8/2010 | Shelton, IV et al. |
| 7,776,060 B2 | 8/2010 | Mooradian et al. |
| 7,780,055 B2 | 8/2010 | Scirica et al. |
| 7,784,662 B2 | 8/2010 | Wales et al. |
| 7,789,283 B2 | 9/2010 | Shah |
| 7,789,889 B2 | 9/2010 | Zubik et al. |
| 7,793,812 B2 | 9/2010 | Moore et al. |
| 7,793,814 B2 | 9/2010 | Racenet et al. |
| 7,794,475 B2 | 9/2010 | Hess et al. |
| 7,798,385 B2 | 9/2010 | Boyden et al. |
| 7,798,386 B2 | 9/2010 | Schall et al. |
| 7,799,039 B2 | 9/2010 | Shelton, IV et al. |
| 7,810,690 B2 | 10/2010 | Bilotti et al. |
| 7,810,692 B2 | 10/2010 | Hall et al. |
| 7,810,693 B2 | 10/2010 | Broehl et al. |
| 7,815,090 B2 | 10/2010 | Marczyk |
| 7,815,091 B2 | 10/2010 | Marczyk |
| 7,815,092 B2 | 10/2010 | Whitman et al. |
| 7,819,296 B2 | 10/2010 | Hueil et al. |
| 7,819,297 B2 | 10/2010 | Doll et al. |
| 7,819,298 B2 | 10/2010 | Hall et al. |
| 7,819,299 B2 | 10/2010 | Shelton, IV et al. |
| 7,819,896 B2 | 10/2010 | Racenet |
| 7,823,760 B2 | 11/2010 | Zemlok et al. |
| 7,823,761 B2 | 11/2010 | Boyden et al. |
| 7,824,426 B2 | 11/2010 | Racenet et al. |
| 7,828,186 B2 | 11/2010 | Wales |
| 7,828,187 B2 | 11/2010 | Green et al. |
| 7,828,188 B2 | 11/2010 | Jankowski |
| 7,828,189 B2 | 11/2010 | Holsten et al. |
| 7,832,408 B2 | 11/2010 | Shelton, IV et al. |
| 7,832,611 B2 | 11/2010 | Boyden et al. |
| 7,832,612 B2 | 11/2010 | Baxter, III et al. |
| 7,834,630 B2 | 11/2010 | Damadian et al. |
| 7,837,079 B2 | 11/2010 | Holsten et al. |
| 7,837,081 B2 | 11/2010 | Holsten et al. |
| 7,841,503 B2 | 11/2010 | Sonnenschein et al. |
| 7,845,533 B2 | 12/2010 | Marczyk et al. |
| 7,845,534 B2 | 12/2010 | Viola et al. |
| 7,845,535 B2 | 12/2010 | Scircia |
| 7,845,537 B2 | 12/2010 | Shelton, IV et al. |
| 7,845,538 B2 | 12/2010 | Whitman |
| 7,850,703 B2 | 12/2010 | Bombard et al. |
| 7,857,183 B2 | 12/2010 | Shelton, IV |
| 7,857,184 B2 | 12/2010 | Viola |
| 7,857,185 B2 | 12/2010 | Swayze et al. |
| 7,857,186 B2 | 12/2010 | Baxter, III et al. |
| 7,861,906 B2 | 1/2011 | Doll et al. |
| 7,861,907 B2 | 1/2011 | Green et al. |
| 7,866,524 B2 | 1/2011 | Krehel |
| 7,866,525 B2 | 1/2011 | Scirica |
| 7,866,526 B2 | 1/2011 | Green et al. |
| 7,866,527 B2 | 1/2011 | Hall et al. |
| 7,866,528 B2 | 1/2011 | Olson et al. |
| 7,870,989 B2 | 1/2011 | Viola et al. |
| 7,886,952 B2 | 2/2011 | Scirica et al. |
| 7,891,532 B2 | 2/2011 | Mastri et al. |
| 7,891,533 B2 | 2/2011 | Green et al. |
| 7,891,534 B2 | 2/2011 | Wenchell et al. |
| 7,896,214 B2 | 3/2011 | Farascioni |
| 7,900,805 B2 | 3/2011 | Shelton, IV et al. |
| 7,901,416 B2 | 3/2011 | Nolan et al. |
| 7,905,380 B2 | 3/2011 | Shelton, IV et al. |
| 7,905,381 B2 | 3/2011 | Baxter, III et al. |
| 7,909,039 B2 | 3/2011 | Hur |
| 7,909,220 B2 | 3/2011 | Viola |
| 7,909,221 B2 | 3/2011 | Viola et al. |
| 7,909,224 B2 | 3/2011 | Prommersberger |
| 7,913,891 B2 | 3/2011 | Doll et al. |
| 7,913,893 B2 | 3/2011 | Mastri et al. |
| 7,914,543 B2 | 3/2011 | Roth et al. |
| 7,918,230 B2 | 4/2011 | Whitman et al. |
| 7,922,061 B2 | 4/2011 | Shelton, IV et al. |
| 7,922,063 B2 | 4/2011 | Zemlok et al. |
| 7,922,064 B2 | 4/2011 | Boyden et al. |
| 7,926,691 B2 | 4/2011 | Viola et al. |
| 7,926,692 B2 | 4/2011 | Racenet et al. |
| 7,934,628 B2 | 5/2011 | Wenchell et al. |
| 7,934,630 B2 | 5/2011 | Shelton, IV et al. |
| 7,934,631 B2 | 5/2011 | Balbierz et al. |
| 7,942,300 B2 | 5/2011 | Rethy et al. |
| 7,942,303 B2 | 5/2011 | Shah |
| 7,950,560 B2 | 5/2011 | Zemlok et al. |
| 7,950,561 B2 | 5/2011 | Aranyi |
| 7,950,562 B2 | 5/2011 | Beardsley et al. |
| 7,954,682 B2 | 6/2011 | Giordano et al. |
| 7,954,683 B1 | 6/2011 | Knodel et al. |
| 7,954,684 B2 | 6/2011 | Boudreaux |
| 7,954,685 B2 | 6/2011 | Viola |
| 7,954,686 B2 | 6/2011 | Baxter, III et al. |
| 7,954,687 B2 | 6/2011 | Zemlok et al. |

(56) References Cited

U.S. PATENT DOCUMENTS

| | | |
|---|---|---|
| 7,959,051 B2 | 6/2011 | Smith et al. |
| 7,963,431 B2 | 6/2011 | Scirica |
| 7,963,432 B2 | 6/2011 | Knodel et al. |
| 7,963,433 B2 | 6/2011 | Whitman et al. |
| 7,967,178 B2 | 6/2011 | Scirica et al. |
| 7,967,179 B2 | 6/2011 | Olson et al. |
| 7,967,180 B2 | 6/2011 | Scirica |
| 7,975,894 B2 | 7/2011 | Boyden et al. |
| 7,980,443 B2 | 7/2011 | Scheib et al. |
| 7,988,026 B2 | 8/2011 | Knodel et al. |
| 7,988,027 B2 | 8/2011 | Olson et al. |
| 7,988,028 B2 | 8/2011 | Farascioni et al. |
| 7,992,758 B2 | 8/2011 | Whitman et al. |
| 7,997,468 B2 | 8/2011 | Farascioni |
| 7,997,469 B2 | 8/2011 | Olson et al. |
| 8,002,795 B2 | 8/2011 | Beetel |
| 8,006,885 B2 | 8/2011 | Marczyk |
| 8,006,887 B2 | 8/2011 | Marczyk |
| 8,007,505 B2 | 8/2011 | Weller et al. |
| 8,007,513 B2 | 8/2011 | Nalagatla et al. |
| 8,011,550 B2 | 9/2011 | Aranyi et al. |
| 8,011,551 B2 | 9/2011 | Marczyk et al. |
| 8,011,552 B2 | 9/2011 | Ivanko |
| 8,011,553 B2 | 9/2011 | Mastri et al. |
| 8,011,555 B2 | 9/2011 | Tarinelli et al. |
| 8,012,170 B2 | 9/2011 | Whitman et al. |
| 8,015,976 B2 | 9/2011 | Shah |
| 8,016,177 B2 | 9/2011 | Bettuchi et al. |
| 8,016,178 B2 | 9/2011 | Olson et al. |
| 8,020,742 B2 | 9/2011 | Marczyk |
| 8,020,743 B2 | 9/2011 | Shelton, IV |
| 8,028,882 B2 | 10/2011 | Viola |
| 8,028,883 B2 | 10/2011 | Stopek |
| 8,028,884 B2 | 10/2011 | Sniffin et al. |
| 8,033,438 B2 | 10/2011 | Scirica |
| 8,033,440 B2 | 10/2011 | Wenchell et al. |
| 8,033,441 B2 | 10/2011 | Marczyk |
| 8,033,442 B2 | 10/2011 | Racenet et al. |
| 8,034,077 B2 | 10/2011 | Smith et al. |
| 8,038,044 B2 | 10/2011 | Viola |
| 8,038,045 B2 | 10/2011 | Bettuchi et al. |
| 8,052,024 B2 | 11/2011 | Viola et al. |
| 8,056,787 B2 | 11/2011 | Boudreaux et al. |
| 8,056,788 B2 | 11/2011 | Mastri et al. |
| 8,056,791 B2 | 11/2011 | Whitman |
| 8,061,577 B2 | 11/2011 | Racenet et al. |
| 8,066,166 B2 | 11/2011 | Demmy et al. |
| 8,070,033 B2 | 12/2011 | Milliman et al. |
| 8,070,034 B1 | 12/2011 | Knodel |
| 8,070,035 B2 | 12/2011 | Holsten et al. |
| 8,074,858 B2 | 12/2011 | Marczyk |
| 8,074,859 B2 | 12/2011 | Kostrzewski |
| 8,074,862 B2 | 12/2011 | Shah |
| 8,083,118 B2 | 12/2011 | Milliman et al. |
| 8,083,119 B2 | 12/2011 | Prommersberger |
| 8,083,120 B2 | 12/2011 | Shelton, IV et al. |
| 8,087,563 B2 | 1/2012 | Milliman et al. |
| 8,091,753 B2 | 1/2012 | Viola |
| 8,091,754 B2 | 1/2012 | Ehrenfels et al. |
| 8,091,756 B2 | 1/2012 | Viola |
| 8,092,493 B2 | 1/2012 | Marczyk |
| 8,096,459 B2 | 1/2012 | Ortiz et al. |
| 8,096,460 B2 | 1/2012 | Blier et al. |
| 8,100,309 B2 | 1/2012 | Marczyk |
| 8,100,310 B2 | 1/2012 | Zemlok |
| 8,102,008 B2 | 1/2012 | Wells |
| 8,113,405 B2 | 2/2012 | Milliman |
| 8,113,406 B2 | 2/2012 | Holsten et al. |
| 8,113,407 B2 | 2/2012 | Holsten et al. |
| 8,113,408 B2 | 2/2012 | Wenchell et al. |
| 8,113,409 B2 | 2/2012 | Cohen et al. |
| 8,113,410 B2 | 2/2012 | Hall et al. |
| 8,123,101 B2 | 2/2012 | Racenet et al. |
| 8,127,975 B2 | 3/2012 | Olson et al. |
| 8,127,976 B2 | 3/2012 | Scirica et al. |
| 8,132,703 B2 | 3/2012 | Milliman et al. |
| 8,132,705 B2 | 3/2012 | Viola et al. |
| 8,132,706 B2 | 3/2012 | Marczyk et al. |
| 8,136,713 B2 | 3/2012 | Hathaway et al. |
| 8,141,762 B2 | 3/2012 | Bedi et al. |
| 8,152,041 B2 | 4/2012 | Kostrzewski |
| 8,157,148 B2 | 4/2012 | Scirica |
| 8,157,150 B2 | 4/2012 | Viola et al. |
| 8,157,151 B2 | 4/2012 | Ingmanson et al. |
| 8,157,152 B2 | 4/2012 | Holsten et al. |
| 8,162,197 B2 | 4/2012 | Mastri et al. |
| 8,167,185 B2 | 5/2012 | Shelton, IV et al. |
| 8,167,186 B2 | 5/2012 | Racenet et al. |
| 8,172,121 B2 | 5/2012 | Krehel |
| 8,172,124 B2 | 5/2012 | Shelton, IV et al. |
| 8,181,837 B2 | 5/2012 | Roy |
| 8,186,555 B2 | 5/2012 | Shelton, IV et al. |
| 8,186,557 B2 | 5/2012 | Cohen et al. |
| 8,186,558 B2 | 5/2012 | Sapienza |
| 8,186,559 B1 | 5/2012 | Whitman |
| 8,186,560 B2 | 5/2012 | Hess et al. |
| 8,193,044 B2 | 6/2012 | Kenneth |
| 8,196,795 B2 | 6/2012 | Moore et al. |
| 8,196,796 B2 | 6/2012 | Shelton, IV et al. |
| 8,201,721 B2 | 6/2012 | Zemlok et al. |
| 8,205,619 B2 | 6/2012 | Shah et al. |
| 8,205,780 B2 | 6/2012 | Sorrentino et al. |
| 8,205,781 B2 | 6/2012 | Baxter, III et al. |
| 8,210,412 B2 | 7/2012 | Marczyk |
| 8,210,416 B2 | 7/2012 | Milliman et al. |
| 8,215,532 B2 | 7/2012 | Marczyk |
| 8,216,236 B2 | 7/2012 | Heinrich et al. |
| 8,220,688 B2 | 7/2012 | Laurent et al. |
| 8,220,690 B2 | 7/2012 | Hess et al. |
| 8,225,979 B2 | 7/2012 | Farascioni et al. |
| 8,231,040 B2 | 7/2012 | Zemlok et al. |
| 8,231,041 B2 | 7/2012 | Marczyk et al. |
| 8,235,272 B2 | 8/2012 | Nicholas et al. |
| 8,235,273 B2 | 8/2012 | Olson et al. |
| 8,235,274 B2 | 8/2012 | Cappola |
| 8,236,010 B2 | 8/2012 | Ortiz et al. |
| 8,240,536 B2 | 8/2012 | Marczyk |
| 8,240,537 B2 | 8/2012 | Marczyk |
| 8,241,322 B2 | 8/2012 | Whitman et al. |
| 8,245,897 B2 | 8/2012 | Tzakis et al. |
| 8,245,898 B2 | 8/2012 | Smith et al. |
| 8,245,899 B2 | 8/2012 | Swensgard et al. |
| 8,245,931 B2 | 8/2012 | Shigeta |
| 8,252,009 B2 | 8/2012 | Weller et al. |
| 8,256,653 B2 | 9/2012 | Farascioni |
| 8,256,654 B2 | 9/2012 | Bettuchi et al. |
| 8,256,655 B2 | 9/2012 | Sniffin et al. |
| 8,256,656 B2 | 9/2012 | Milliman et al. |
| 8,267,300 B2 | 9/2012 | Boudreaux |
| 8,272,551 B2 | 9/2012 | Knodel et al. |
| 8,272,553 B2 | 9/2012 | Mastri et al. |
| 8,272,554 B2 | 9/2012 | Whitman et al. |
| 8,276,594 B2 | 10/2012 | Shah |
| 8,276,801 B2 | 10/2012 | Zemlok et al. |
| 8,281,973 B2 | 10/2012 | Wenchell et al. |
| 8,286,847 B2 | 10/2012 | Taylor |
| 8,286,848 B2 | 10/2012 | Wenchell et al. |
| 8,286,850 B2 | 10/2012 | Viola |
| 8,292,146 B2 | 10/2012 | Holsten et al. |
| 8,292,147 B2 | 10/2012 | Viola |
| 8,292,148 B2 | 10/2012 | Viola |
| 8,292,149 B2 | 10/2012 | Ivanko |
| 8,292,150 B2 | 10/2012 | Bryant |
| 8,292,151 B2 | 10/2012 | Viola |
| 8,292,152 B2 | 10/2012 | Milliman et al. |
| 8,292,153 B2 | 10/2012 | Jankowski |
| 8,292,154 B2 | 10/2012 | Marczyk |
| 8,292,155 B2 | 10/2012 | Shelton, IV et al. |
| 8,292,156 B2 | 10/2012 | Kostrzewski |
| 8,292,158 B2 | 10/2012 | Sapienza |
| 8,308,040 B2 | 11/2012 | Huang et al. |
| 8,308,041 B2 | 11/2012 | Kostrzewski |
| 8,308,042 B2 | 11/2012 | Aranyi |
| 8,308,043 B2 | 11/2012 | Bindra et al. |

(56) References Cited

U.S. PATENT DOCUMENTS

| | | |
|---|---|---|
| 8,308,044 B2 | 11/2012 | Viola |
| 8,308,046 B2 | 11/2012 | Prommersberger |
| 8,308,757 B2 | 11/2012 | Hillstead et al. |
| 8,317,070 B2 | 11/2012 | Hueil et al. |
| 8,317,071 B1 | 11/2012 | Knodel |
| 8,322,455 B2 | 12/2012 | Shelton, IV et al. |
| 8,322,589 B2 | 12/2012 | Boudreaux |
| 8,328,061 B2 | 12/2012 | Kasvikis |
| 8,328,065 B2 | 12/2012 | Shah |
| 8,333,313 B2 | 12/2012 | Boudreaux et al. |
| 8,336,751 B2 | 12/2012 | Scirica |
| 8,336,753 B2 | 12/2012 | Olson et al. |
| 8,336,754 B2 | 12/2012 | Cappola et al. |
| 8,342,377 B2 | 1/2013 | Milliman et al. |
| 8,342,378 B2 | 1/2013 | Marczyk et al. |
| 8,342,379 B2 | 1/2013 | Whitman et al. |
| 8,342,380 B2 | 1/2013 | Viola |
| 8,348,123 B2 | 1/2013 | Scirica et al. |
| 8,348,124 B2 | 1/2013 | Scirica |
| 8,348,125 B2 | 1/2013 | Viola et al. |
| 8,348,126 B2 | 1/2013 | Olson et al. |
| 8,348,127 B2 | 1/2013 | Marczyk |
| 8,348,129 B2 | 1/2013 | Bedi et al. |
| 8,348,130 B2 | 1/2013 | Shah et al. |
| 8,348,131 B2 | 1/2013 | Omaits et al. |
| 8,353,437 B2 | 1/2013 | Boudreaux |
| 8,353,440 B2 | 1/2013 | Whitman et al. |
| 8,356,740 B1 | 1/2013 | Knodel |
| 8,357,174 B2 | 1/2013 | Roth et al. |
| 8,360,294 B2 | 1/2013 | Scirica |
| 8,360,297 B2 | 1/2013 | Shelton, IV et al. |
| 8,360,298 B2 | 1/2013 | Farascioni et al. |
| 8,360,299 B2 | 1/2013 | Zemlok et al. |
| 8,365,971 B1 | 2/2013 | Knodel |
| 8,365,972 B2 | 2/2013 | Aranyi et al. |
| 8,365,973 B1 | 2/2013 | White et al. |
| 8,365,976 B2 | 2/2013 | Hess et al. |
| 8,371,491 B2 | 2/2013 | Huitema et al. |
| 8,371,492 B2 | 2/2013 | Aranyi et al. |
| 8,371,493 B2 | 2/2013 | Aranyi et al. |
| 8,381,828 B2 | 2/2013 | Whitman et al. |
| 8,381,961 B2 | 2/2013 | Holsten et al. |
| 8,387,848 B2 | 3/2013 | Johnson et al. |
| 8,387,849 B2 | 3/2013 | Buesseler et al. |
| 8,387,850 B2 | 3/2013 | Hathaway et al. |
| 8,388,652 B2 | 3/2013 | Viola |
| 8,393,513 B2 | 3/2013 | Jankowski |
| 8,393,514 B2 | 3/2013 | Shelton, IV et al. |
| 8,393,516 B2 | 3/2013 | Kostrzewski |
| 8,397,971 B2 | 3/2013 | Yates et al. |
| 8,397,972 B2 | 3/2013 | Kostrzewski |
| 8,403,195 B2 | 3/2013 | Beardsley et al. |
| 8,403,196 B2 | 3/2013 | Beardsley et al. |
| 8,403,197 B2 | 3/2013 | Vidal et al. |
| 8,403,198 B2 | 3/2013 | Sorrentino et al. |
| 8,403,956 B1 | 3/2013 | Thompson et al. |
| 8,408,439 B2 | 4/2013 | Huang et al. |
| 8,408,440 B2 | 4/2013 | Olson et al. |
| 8,408,442 B2 | 4/2013 | Racenet et al. |
| 8,413,868 B2 | 4/2013 | Cappola |
| 8,413,869 B2 | 4/2013 | Heinrich |
| 8,413,871 B2 | 4/2013 | Racenet et al. |
| 8,418,904 B2 | 4/2013 | Wenchell et al. |
| 8,418,905 B2 | 4/2013 | Milliman |
| 8,418,906 B2 | 4/2013 | Farascioni et al. |
| 8,418,907 B2 | 4/2013 | Johnson et al. |
| 8,418,908 B1 | 4/2013 | Beardsley |
| 8,419,768 B2 | 4/2013 | Marczyk |
| 8,424,735 B2 | 4/2013 | Viola et al. |
| 8,424,736 B2 | 4/2013 | Scirica et al. |
| 8,424,737 B2 | 4/2013 | Scirica |
| 8,424,739 B2 | 4/2013 | Racenet et al. |
| 8,424,740 B2 | 4/2013 | Shelton, IV et al. |
| 8,439,244 B2 | 5/2013 | Holcomb et al. |
| 8,439,245 B2 | 5/2013 | Knodel et al. |
| 8,439,246 B1 | 5/2013 | Knodel |
| 8,444,036 B2 | 5/2013 | Shelton, IV |
| 8,444,037 B2 | 5/2013 | Nicholas et al. |
| 8,444,038 B2 | 5/2013 | Farascioni et al. |
| 8,448,832 B2 | 5/2013 | Viola et al. |
| 8,453,652 B2 | 6/2013 | Stopek |
| 8,453,905 B2 | 6/2013 | Holcomb et al. |
| 8,453,906 B2 | 6/2013 | Huang et al. |
| 8,453,907 B2 | 6/2013 | Laurent et al. |
| 8,453,908 B2 | 6/2013 | Bedi et al. |
| 8,453,909 B2 | 6/2013 | Olson et al. |
| 8,453,910 B2 | 6/2013 | Bettuchi et al. |
| 8,453,912 B2 | 6/2013 | Mastri et al. |
| 8,453,913 B2 | 6/2013 | Milliman |
| 8,453,914 B2 | 6/2013 | Laurent et al. |
| 8,454,628 B2 | 6/2013 | Smith et al. |
| 8,459,520 B2 | 6/2013 | Giordano et al. |
| 8,459,521 B2 | 6/2013 | Zemlok et al. |
| 8,459,522 B2 | 6/2013 | Marczyk |
| 8,459,523 B2 | 6/2013 | Whitman |
| 8,459,524 B2 | 6/2013 | Pribanic et al. |
| 8,459,525 B2 | 6/2013 | Yates et al. |
| 8,464,922 B2 | 6/2013 | Marczyk |
| 8,464,923 B2 | 6/2013 | Shelton, IV |
| 8,469,252 B2 | 6/2013 | Holcomb et al. |
| 8,469,254 B2 | 6/2013 | Czernik et al. |
| 8,474,677 B2 | 7/2013 | Woodard, Jr. et al. |
| 8,479,967 B2 | 7/2013 | Marczyk |
| 8,479,968 B2 | 7/2013 | Hodgkinson et al. |
| 8,479,969 B2 | 7/2013 | Shelton, IV |
| 8,485,412 B2 | 7/2013 | Shelton, IV et al. |
| 8,490,852 B2 | 7/2013 | Viola |
| 8,496,152 B2 | 7/2013 | Viola |
| 8,496,154 B2 | 7/2013 | Marczyk et al. |
| 8,496,156 B2 | 7/2013 | Sniffin et al. |
| 8,496,683 B2 | 7/2013 | Prommersberger et al. |
| 8,499,993 B2 | 8/2013 | Shelton, IV et al. |
| 8,505,799 B2 | 8/2013 | Viola et al. |
| 8,505,802 B2 | 8/2013 | Viola et al. |
| 8,511,575 B2 | 8/2013 | Cok |
| 8,512,359 B2 | 8/2013 | Whitman et al. |
| 8,512,402 B2 | 8/2013 | Marczyk et al. |
| 8,517,240 B1 | 8/2013 | Mata et al. |
| 8,517,241 B2 | 8/2013 | Nicholas et al. |
| 8,517,243 B2 | 8/2013 | Giordano et al. |
| 8,517,244 B2 | 8/2013 | Shelton, IV et al. |
| 8,523,041 B2 | 9/2013 | Ishitsuki et al. |
| 8,523,042 B2 | 9/2013 | Masiakos et al. |
| 8,523,043 B2 | 9/2013 | Ullrich et al. |
| 8,534,528 B2 | 9/2013 | Shelton, IV |
| 8,540,128 B2 | 9/2013 | Shelton, IV et al. |
| 8,540,129 B2 | 9/2013 | Baxter, III et al. |
| 8,540,130 B2 | 9/2013 | Moore et al. |
| 8,540,131 B2 | 9/2013 | Swayze |
| 8,540,733 B2 | 9/2013 | Whitman et al. |
| 8,544,711 B2 | 10/2013 | Ma et al. |
| 8,550,325 B2 | 10/2013 | Cohen et al. |
| 8,556,151 B2 | 10/2013 | Viola |
| 8,561,870 B2 | 10/2013 | Baxter, III et al. |
| 8,561,873 B2 | 10/2013 | Ingmanson et al. |
| 8,561,874 B2 | 10/2013 | Scirica |
| 8,567,656 B2 | 10/2013 | Shelton, IV et al. |
| 8,573,461 B2 | 11/2013 | Shelton, IV et al. |
| 8,573,463 B2 | 11/2013 | Scirica et al. |
| 8,573,465 B2 | 11/2013 | Shelton, IV |
| 8,579,176 B2 | 11/2013 | Smith et al. |
| 8,579,177 B2 | 11/2013 | Beetel |
| 8,584,919 B2 | 11/2013 | Hueil et al. |
| 8,584,920 B2 | 11/2013 | Hodgkinson |
| 8,590,762 B2 | 11/2013 | Hess et al. |
| 8,596,515 B2 | 12/2013 | Okoniewski |
| 8,597,311 B2 | 12/2013 | Criscuolo et al. |
| 8,602,288 B2 | 12/2013 | Shelton, IV et al. |
| 8,608,045 B2 | 12/2013 | Smith et al. |
| 8,608,046 B2 | 12/2013 | Laurent et al. |
| 8,608,047 B2 | 12/2013 | Holsten et al. |
| 8,613,383 B2 | 12/2013 | Beckman et al. |
| 8,613,384 B2 | 12/2013 | Pastorelli et al. |
| 8,616,427 B2 | 12/2013 | Viola |

(56) References Cited

U.S. PATENT DOCUMENTS

| | | |
|---|---|---|
| 8,616,430 B2 | 12/2013 | Stopek et al. |
| 8,627,994 B2 | 1/2014 | Zemlok et al. |
| 8,628,544 B2 | 1/2014 | Farascioni |
| 8,631,988 B2 | 1/2014 | Viola |
| 8,631,989 B2 | 1/2014 | Aranyi et al. |
| 8,631,991 B2 | 1/2014 | Cropper et al. |
| 8,632,525 B2 | 1/2014 | Kerr et al. |
| 8,632,535 B2 | 1/2014 | Shelton, IV et al. |
| 8,636,187 B2 | 1/2014 | Hueil et al. |
| 8,636,190 B2 | 1/2014 | Zemlok et al. |
| 8,636,192 B2 | 1/2014 | Farascioni et al. |
| 8,636,762 B2 | 1/2014 | Whitman et al. |
| 8,636,766 B2 | 1/2014 | Milliman et al. |
| 8,640,940 B2 | 2/2014 | Ohdaira |
| 8,657,174 B2 | 2/2014 | Yates et al. |
| 8,657,177 B2 | 2/2014 | Scirica et al. |
| 8,657,178 B2 | 2/2014 | Hueil et al. |
| 8,662,371 B2 | 3/2014 | Viola |
| 8,668,129 B2 | 3/2014 | Olson |
| 8,672,206 B2 | 3/2014 | Aranyi et al. |
| 8,672,208 B2 | 3/2014 | Hess et al. |
| 8,672,209 B2 | 3/2014 | Crainich |
| 8,678,263 B2 | 3/2014 | Viola |
| 8,678,990 B2 | 3/2014 | Wazer et al. |
| 8,679,155 B2 | 3/2014 | Knodel et al. |
| 8,684,247 B2 | 4/2014 | Scirica et al. |
| 8,684,249 B2 | 4/2014 | Racenet et al. |
| 8,684,253 B2 | 4/2014 | Giordano et al. |
| 8,690,039 B2 | 4/2014 | Beardsley et al. |
| 8,695,865 B2 | 4/2014 | Smith et al. |
| 8,695,866 B2 | 4/2014 | Leimbach et al. |
| 8,701,958 B2 | 4/2014 | Shelton, IV et al. |
| 8,701,959 B2 | 4/2014 | Shah |
| 8,701,961 B2 | 4/2014 | Ivanko |
| 8,708,213 B2 | 4/2014 | Shelton, IV et al. |
| 8,714,429 B2 | 5/2014 | Demmy |
| 8,715,277 B2 | 5/2014 | Weizman |
| 8,720,766 B2 | 5/2014 | Hess et al. |
| 8,721,630 B2 | 5/2014 | Ortiz et al. |
| 8,727,197 B2 | 5/2014 | Hess et al. |
| 8,727,200 B2 | 5/2014 | Roy |
| 8,733,612 B2 | 5/2014 | Ma |
| 8,740,034 B2 | 6/2014 | Morgan et al. |
| 8,740,039 B2 | 6/2014 | Farascioni |
| 8,746,529 B2 | 6/2014 | Shelton, IV et al. |
| 8,746,530 B2 | 6/2014 | Giordano et al. |
| 8,746,533 B2 | 6/2014 | Whitman |
| 8,746,534 B2 | 6/2014 | Farascioni |
| 8,746,535 B2 | 6/2014 | Shelton, IV et al. |
| 8,747,421 B2 | 6/2014 | Balbierz et al. |
| 8,752,747 B2 | 6/2014 | Shelton, IV et al. |
| 8,752,748 B2 | 6/2014 | Whitman et al. |
| 8,752,749 B2 | 6/2014 | Moore et al. |
| 8,757,465 B2 | 6/2014 | Woodard, Jr. et al. |
| 8,758,391 B2 | 6/2014 | Swayze et al. |
| 8,763,875 B2 | 7/2014 | Morgan et al. |
| 8,763,876 B2 | 7/2014 | Kostrzewski |
| 8,763,877 B2 | 7/2014 | Schall et al. |
| 8,763,879 B2 | 7/2014 | Shelton, IV et al. |
| 8,770,458 B2 | 7/2014 | Scirica |
| 8,777,082 B2 | 7/2014 | Scirica |
| 8,783,541 B2 | 7/2014 | Shelton, IV et al. |
| 8,783,542 B2 | 7/2014 | Riestenberg et al. |
| 8,789,737 B2 | 7/2014 | Hodgkinson et al. |
| 8,789,738 B2 | 7/2014 | Knodel et al. |
| 8,789,739 B2 | 7/2014 | Swensgard |
| 8,800,838 B2 | 8/2014 | Shelton, IV |
| 8,800,840 B2 | 8/2014 | Jankowski |
| 8,800,841 B2 | 8/2014 | Ellerhorst et al. |
| 8,808,311 B2 | 8/2014 | Heinrich et al. |
| 8,814,024 B2 | 8/2014 | Woodard, Jr. et al. |
| 8,814,025 B2 | 8/2014 | Miller et al. |
| 8,820,603 B2 | 9/2014 | Shelton, IV et al. |
| 8,820,605 B2 | 9/2014 | Shelton, IV |
| 8,820,606 B2 | 9/2014 | Hodgkinson |
| 8,820,607 B2 | 9/2014 | Marczyk |
| 8,827,133 B2 | 9/2014 | Shelton, IV et al. |
| 8,827,134 B2 | 9/2014 | Viola et al. |
| 8,833,631 B2 | 9/2014 | Munro, III et al. |
| 8,833,632 B2 | 9/2014 | Swensgard |
| 8,840,003 B2 | 9/2014 | Morgan et al. |
| 8,840,603 B2 | 9/2014 | Shelton, IV et al. |
| 8,844,788 B2 | 9/2014 | Knodel |
| 8,851,354 B2 | 10/2014 | Swensgard et al. |
| 8,851,355 B2 | 10/2014 | Aranyi et al. |
| 8,857,693 B2 | 10/2014 | Schuckmann et al. |
| 8,864,007 B2 | 10/2014 | Widenhouse et al. |
| 8,864,009 B2 | 10/2014 | Shelton, IV et al. |
| 8,864,010 B2 | 10/2014 | Williams |
| 8,870,050 B2 | 10/2014 | Hodgkinson |
| 8,875,971 B2 | 11/2014 | Hall et al. |
| 8,875,972 B2 | 11/2014 | Weisenburgh, II et al. |
| 8,893,949 B2 | 11/2014 | Shelton, IV et al. |
| 8,893,950 B2 | 11/2014 | Marczyk |
| 8,899,461 B2 | 12/2014 | Farascioni |
| 8,899,462 B2 | 12/2014 | Kostrzewski et al. |
| 8,899,463 B2 | 12/2014 | Schall et al. |
| 8,899,464 B2 | 12/2014 | Hueil et al. |
| 8,900,616 B2 | 12/2014 | Belcheva et al. |
| 8,920,435 B2 | 12/2014 | Smith et al. |
| 8,925,782 B2 | 1/2015 | Shelton, IV |
| 8,926,598 B2 | 1/2015 | Mollere et al. |
| 8,931,681 B2 | 1/2015 | Kostrzewski |
| 8,931,682 B2 | 1/2015 | Timm et al. |
| 8,931,693 B1 | 1/2015 | Kumar et al. |
| 8,955,732 B2 | 2/2015 | Zemlok et al. |
| 8,958,429 B2 | 2/2015 | Shukla et al. |
| 8,960,517 B2 | 2/2015 | Lee |
| 8,960,520 B2 | 2/2015 | McCuen |
| 8,967,443 B2 | 3/2015 | McCuen |
| 8,967,446 B2 | 3/2015 | Beardsley et al. |
| 8,973,803 B2 | 3/2015 | Hall et al. |
| 8,978,954 B2 | 3/2015 | Shelton, IV et al. |
| 8,978,956 B2 | 3/2015 | Schall et al. |
| 8,991,677 B2 | 3/2015 | Moore et al. |
| 8,991,678 B2 | 3/2015 | Wellman et al. |
| 8,998,058 B2 | 4/2015 | Moore et al. |
| 8,998,060 B2 | 4/2015 | Bruewer et al. |
| 9,005,230 B2 | 4/2015 | Yates et al. |
| 9,010,606 B2 | 4/2015 | Aranyi et al. |
| 9,010,607 B2 | 4/2015 | Kostrzewski |
| 9,010,610 B2 | 4/2015 | Hodgkinson |
| 9,016,539 B2 | 4/2015 | Kostrzewski et al. |
| 9,016,541 B2 | 4/2015 | Viola et al. |
| 9,016,542 B2 | 4/2015 | Shelton, IV et al. |
| 9,016,544 B2 | 4/2015 | Hodgkinson et al. |
| 9,016,545 B2 | 4/2015 | Aranyi et al. |
| 9,016,546 B2 | 4/2015 | Demmy et al. |
| 9,017,371 B2 | 4/2015 | Whitman et al. |
| 9,022,271 B2 | 5/2015 | Scirica |
| 9,027,817 B2 | 5/2015 | Milliman et al. |
| 9,033,203 B2 | 5/2015 | Woodard, Jr. et al. |
| 9,044,228 B2 | 6/2015 | Woodard, Jr. et al. |
| 9,044,229 B2 | 6/2015 | Scheib et al. |
| 9,050,084 B2 | 6/2015 | Schmid et al. |
| 9,055,941 B2 | 6/2015 | Schmid et al. |
| 9,060,770 B2 | 6/2015 | Shelton, IV et al. |
| 9,072,535 B2 | 7/2015 | Shelton, IV et al. |
| 9,084,601 B2 | 7/2015 | Moore et al. |
| 9,084,602 B2 | 7/2015 | Gleiman |
| 9,089,326 B2 | 7/2015 | Krumanaker et al. |
| 9,095,339 B2 | 8/2015 | Moore et al. |
| 9,101,359 B2 | 8/2015 | Smith et al. |
| 9,107,663 B2 | 8/2015 | Swensgard |
| 9,107,664 B2 | 8/2015 | Marczyk |
| 9,107,667 B2 | 8/2015 | Hodgkinson |
| 9,113,862 B2 | 8/2015 | Morgan et al. |
| 9,113,864 B2 | 8/2015 | Morgan et al. |
| 9,113,870 B2 | 8/2015 | Viola |
| 9,113,872 B2 | 8/2015 | Viola |
| 9,113,880 B2 | 8/2015 | Zemlok et al. |
| 9,125,649 B2 | 9/2015 | Bruewer et al. |
| 9,138,225 B2 | 9/2015 | Huang et al. |
| 9,155,537 B2 | 10/2015 | Katre et al. |

(56) References Cited

U.S. PATENT DOCUMENTS

| | | |
|---|---|---|
| 9,179,912 B2 | 11/2015 | Yates et al. |
| 9,192,378 B2 | 11/2015 | Aranyi et al. |
| 9,192,379 B2 | 11/2015 | Aranyi et al. |
| 9,192,384 B2 | 11/2015 | Bettuchi |
| 9,198,644 B2 | 12/2015 | Balek et al. |
| 9,198,660 B2 | 12/2015 | Hodgkinson |
| 9,198,661 B2 | 12/2015 | Swensgard |
| 9,198,662 B2 | 12/2015 | Barton et al. |
| 9,204,876 B2 | 12/2015 | Cappola et al. |
| 9,204,877 B2 | 12/2015 | Whitman et al. |
| 9,204,880 B2 | 12/2015 | Baxter, III et al. |
| 9,216,019 B2 | 12/2015 | Schmid et al. |
| 9,216,020 B2 | 12/2015 | Zhang et al. |
| 9,220,500 B2 | 12/2015 | Swayze et al. |
| 9,220,501 B2 | 12/2015 | Baxter, III et al. |
| 9,220,502 B2 | 12/2015 | Zemlok et al. |
| 9,232,941 B2 | 1/2016 | Mandakolathur Vasudevan et al. |
| 9,232,944 B2 | 1/2016 | Cappola et al. |
| 9,237,891 B2 | 1/2016 | Shelton, IV |
| 9,237,892 B2 | 1/2016 | Hodgkinson |
| 9,254,180 B2 | 2/2016 | Huitema et al. |
| 9,265,585 B2 | 2/2016 | Wingardner et al. |
| 9,271,728 B2 | 3/2016 | Gupta et al. |
| 9,272,406 B2 | 3/2016 | Aronhalt et al. |
| 9,277,919 B2 | 3/2016 | Timmer et al. |
| 9,282,962 B2 | 3/2016 | Schmid et al. |
| 9,283,054 B2 | 3/2016 | Morgan et al. |
| 9,289,209 B2 | 3/2016 | Gurumurthy et al. |
| 9,289,210 B2 | 3/2016 | Baxter, III et al. |
| 9,289,225 B2 | 3/2016 | Shelton, IV et al. |
| 9,295,464 B2 | 3/2016 | Shelton, IV et al. |
| 9,295,465 B2 | 3/2016 | Farascioni |
| 9,295,466 B2 | 3/2016 | Hodgkinson et al. |
| 9,301,752 B2 | 4/2016 | Mandakolathur Vasudevan et al. |
| 9,301,753 B2 | 4/2016 | Aldridge et al. |
| 9,301,757 B2 | 4/2016 | Williams |
| 9,301,759 B2 | 4/2016 | Spivey et al. |
| 9,307,965 B2 | 4/2016 | Ming et al. |
| 9,307,986 B2 | 4/2016 | Hall et al. |
| 9,307,989 B2 | 4/2016 | Shelton, IV et al. |
| 9,314,246 B2 | 4/2016 | Shelton, IV et al. |
| 9,320,518 B2 | 4/2016 | Henderson et al. |
| 9,320,521 B2 | 4/2016 | Shelton, IV et al. |
| 9,320,523 B2 | 4/2016 | Shelton, IV et al. |
| 9,326,767 B2 | 5/2016 | Koch, Jr. et al. |
| 9,326,771 B2 | 5/2016 | Baxter, III et al. |
| 9,332,987 B2 | 5/2016 | Leimbach et al. |
| 9,345,477 B2 | 5/2016 | Anim et al. |
| 9,345,478 B2 | 5/2016 | Knodel |
| 9,345,479 B2 | 5/2016 | Racenet et al. |
| 9,345,481 B2 | 5/2016 | Hall et al. |
| 9,345,780 B2 | 5/2016 | Manoharan et al. |
| 9,351,726 B2 | 5/2016 | Leimbach |
| 9,351,727 B2 | 5/2016 | Leimbach et al. |
| 9,351,732 B2 | 5/2016 | Hodgkinson |
| 9,358,003 B2 | 6/2016 | Hall et al. |
| 9,364,217 B2 | 6/2016 | Kostrzewski et al. |
| 9,364,218 B2 | 6/2016 | Scirica |
| 9,364,219 B2 | 6/2016 | Olson et al. |
| 9,364,220 B2 | 6/2016 | Williams |
| 9,364,227 B2 | 6/2016 | Kostrzewski |
| 9,364,231 B2 | 6/2016 | Wenchell |
| 9,364,233 B2 | 6/2016 | Alexander, III et al. |
| 9,370,358 B2 | 6/2016 | Shelton, IV et al. |
| 9,370,362 B2 | 6/2016 | Petty et al. |
| 9,386,983 B2 | 7/2016 | Swensgard et al. |
| 9,386,984 B2 | 7/2016 | Aronhalt et al. |
| 9,386,988 B2 | 7/2016 | Baxter, III et al. |
| 9,393,018 B2 | 7/2016 | Wang et al. |
| 9,398,911 B2 | 7/2016 | Auld |
| 9,402,604 B2 | 8/2016 | Williams et al. |
| 9,402,627 B2 | 8/2016 | Stevenson et al. |
| 9,421,014 B2 | 8/2016 | Ingmanson et al. |
| 9,433,419 B2 | 9/2016 | Gonzalez et al. |
| 9,433,420 B2 | 9/2016 | Hodgkinson |
| 9,445,810 B2 | 9/2016 | Cappola |
| 9,445,813 B2 | 9/2016 | Shelton, IV et al. |
| 9,451,959 B2 | 9/2016 | Patankar et al. |
| 9,468,438 B2 | 10/2016 | Baber et al. |
| 9,468,439 B2 | 10/2016 | Cappola et al. |
| 9,480,476 B2 | 11/2016 | Aldridge et al. |
| 9,480,492 B2 | 11/2016 | Aranyi et al. |
| 9,492,171 B2 | 11/2016 | Patenaude |
| 9,498,212 B2 | 11/2016 | Racenet et al. |
| 9,498,219 B2 | 11/2016 | Moore et al. |
| 9,510,827 B2 | 12/2016 | Kostrzewski |
| 9,517,065 B2 | 12/2016 | Simms et al. |
| 9,517,066 B2 | 12/2016 | Racenet et al. |
| 9,522,002 B2 | 12/2016 | Chowaniec et al. |
| 9,539,007 B2 | 1/2017 | Dhakad et al. |
| 9,549,735 B2 | 1/2017 | Shelton, IV et al. |
| 9,554,794 B2 | 1/2017 | Baber |
| 9,561,029 B2 | 2/2017 | Scheib et al. |
| 9,561,031 B2 | 2/2017 | Heinrich et al. |
| 9,566,065 B2 | 2/2017 | Knodel |
| 9,572,576 B2 | 2/2017 | Hodgkinson et al. |
| 9,579,101 B2 | 2/2017 | Whitman et al. |
| 9,585,657 B2 | 3/2017 | Shelton, IV et al. |
| 9,585,662 B2 | 3/2017 | Shelton, IV et al. |
| 9,597,077 B2 | 3/2017 | Hodgkinson |
| 9,610,080 B2 | 4/2017 | Whitfield et al. |
| 9,615,825 B2 | 4/2017 | Viola |
| 9,615,826 B2 | 4/2017 | Shelton, IV et al. |
| 9,622,746 B2 | 4/2017 | Simms |
| 9,629,623 B2 | 4/2017 | Lytle, IV et al. |
| 9,629,626 B2 | 4/2017 | Soltz et al. |
| 9,629,628 B2 | 4/2017 | Aranyi |
| 9,629,629 B2 | 4/2017 | Leimbach et al. |
| 9,642,620 B2 | 5/2017 | Baxter, III |
| 9,649,109 B2 | 5/2017 | Ranucci et al. |
| 9,655,613 B2 | 5/2017 | Schaller |
| 9,662,108 B2 | 5/2017 | Williams |
| 9,668,728 B2 | 6/2017 | Williams et al. |
| 9,668,732 B2 | 6/2017 | Patel et al. |
| 9,675,351 B2 | 6/2017 | Hodgkinson et al. |
| 9,681,870 B2 | 6/2017 | Baxter, III et al. |
| 9,687,230 B2 | 6/2017 | Leimbach et al. |
| 9,687,233 B2 | 6/2017 | Fernandez et al. |
| 9,693,772 B2 | 7/2017 | Ingmanson et al. |
| 9,700,309 B2 | 7/2017 | Jaworek |
| 9,700,319 B2 | 7/2017 | Motooka et al. |
| 9,706,993 B2 | 7/2017 | Hessler et al. |
| 9,713,474 B2 | 7/2017 | Lorenz |
| 9,717,497 B2 | 8/2017 | Zerkle et al. |
| 9,717,498 B2 | 8/2017 | Aranyi et al. |
| 9,724,092 B2 | 8/2017 | Baxter, III et al. |
| 9,724,095 B2 | 8/2017 | Gupta et al. |
| 9,763,662 B2 | 9/2017 | Shelton, IV et al. |
| 9,770,245 B2 | 9/2017 | Swayze et al. |
| 9,775,610 B2 | 10/2017 | Nicholas et al. |
| 9,775,635 B2 | 10/2017 | Takei |
| 9,782,169 B2 | 10/2017 | Kimsey |
| 9,782,173 B2 | 10/2017 | Mozdzierz |
| 9,795,379 B2 | 10/2017 | Leimbach et al. |
| 9,795,384 B2 | 10/2017 | Weaner et al. |
| 9,808,246 B2 | 11/2017 | Shelton, IV |
| 9,808,248 B2 | 11/2017 | Hoffman |
| 9,808,249 B2 | 11/2017 | Shelton, IV |
| 9,820,741 B2 | 11/2017 | Kostrzewski |
| 9,820,742 B2 | 11/2017 | Covach et al. |
| 9,827,002 B2 | 11/2017 | Hausen et al. |
| 9,839,420 B2 | 12/2017 | Shelton, IV |
| 9,839,421 B2 | 12/2017 | Zerkle et al. |
| 9,839,428 B2 | 12/2017 | Baxter, III et al. |
| 9,855,038 B2 | 1/2018 | Smith et al. |
| 9,855,040 B2 | 1/2018 | Kostrzewski |
| 9,861,358 B2 | 1/2018 | Marczyk et al. |
| 9,861,359 B2 | 1/2018 | Shelton, IV et al. |
| 9,867,612 B2 | 1/2018 | Parihar et al. |
| 9,867,613 B2 | 1/2018 | Marczyk et al. |
| 9,867,615 B2 | 1/2018 | Fanelli et al. |
| 9,872,683 B2 | 1/2018 | Hopkins |
| 9,883,860 B2 | 2/2018 | Leimbach et al. |
| 9,901,342 B2 | 2/2018 | Shelton, IV et al. |

(56) References Cited

U.S. PATENT DOCUMENTS

| | | |
|---|---|---|
| 9,913,646 B2 | 3/2018 | Shelton, IV |
| 9,918,714 B2 | 3/2018 | Gibbons, Jr. |
| 9,918,717 B2 | 3/2018 | Czernik |
| 9,924,941 B2 | 3/2018 | Burbank |
| 9,924,942 B2 | 3/2018 | Swayze et al. |
| 9,936,951 B2 | 4/2018 | Hufnagel et al. |
| 9,936,954 B2 | 4/2018 | Shelton, IV et al. |
| 9,943,311 B2 | 4/2018 | Scirica et al. |
| 9,949,737 B2 | 4/2018 | Zergiebel et al. |
| 9,955,966 B2 | 5/2018 | Zergiebel |
| 9,968,354 B2 | 5/2018 | Shelton, IV et al. |
| 9,980,724 B2 | 5/2018 | Farascioni et al. |
| 9,987,012 B2 | 6/2018 | Shah |
| 9,987,099 B2 | 6/2018 | Chen et al. |
| 9,993,248 B2 | 6/2018 | Shelton, IV et al. |
| 9,993,258 B2 | 6/2018 | Shelton, IV et al. |
| 10,004,497 B2 | 6/2018 | Overmyer et al. |
| 10,004,505 B2 | 6/2018 | Moore et al. |
| 10,034,668 B2 | 7/2018 | Ebner |
| 10,039,532 B2 | 8/2018 | Srinivas et al. |
| 10,039,545 B2 | 8/2018 | Sadowski et al. |
| 10,045,782 B2 | 8/2018 | Murthy Aravalli |
| 10,052,044 B2 | 8/2018 | Shelton, IV et al. |
| 10,058,963 B2 | 8/2018 | Shelton, IV et al. |
| 10,064,622 B2 | 9/2018 | Murthy Aravalli |
| 10,076,325 B2 | 9/2018 | Huang et al. |
| 10,085,750 B2 | 10/2018 | Zergiebel et al. |
| 10,092,290 B2 | 10/2018 | Mgit et al. |
| 10,092,292 B2 | 10/2018 | Boudreaux et al. |
| 10,111,657 B2 | 10/2018 | McCuen |
| 10,111,665 B2 | 10/2018 | Aranyi |
| 10,117,650 B2 | 11/2018 | Nicholas et al. |
| 10,117,654 B2 | 11/2018 | Ingmanson et al. |
| 10,123,796 B2 | 11/2018 | Westling et al. |
| 10,123,798 B2 | 11/2018 | Baxter, III et al. |
| 10,135,242 B2 | 11/2018 | Baber et al. |
| 10,143,474 B2 | 12/2018 | Bucciaglia et al. |
| 10,172,612 B2 | 1/2019 | Frushour |
| 10,172,615 B2 | 1/2019 | Marczyk et al. |
| 10,172,617 B2 | 1/2019 | Shelton, IV et al. |
| 10,175,127 B2 | 1/2019 | Collins et al. |
| 10,180,463 B2 | 1/2019 | Beckman et al. |
| 10,182,816 B2 | 1/2019 | Shelton, IV et al. |
| 10,206,677 B2 | 2/2019 | Harris et al. |
| 10,213,201 B2 | 2/2019 | Shelton, IV et al. |
| 10,219,804 B2 | 3/2019 | Linder et al. |
| 10,226,239 B2 | 3/2019 | Nicholas et al. |
| 10,226,250 B2 | 3/2019 | Beckman et al. |
| 10,226,254 B2 | 3/2019 | Cabrera et al. |
| 10,245,033 B2 | 4/2019 | Overmyer et al. |
| 10,245,038 B2 | 4/2019 | Hopkins et al. |
| 10,251,725 B2 | 4/2019 | Valentine et al. |
| 10,265,065 B2 | 4/2019 | Shelton, IV et al. |
| 10,265,066 B2 | 4/2019 | Measamer et al. |
| 10,265,074 B2 | 4/2019 | Shelton, IV et al. |
| 10,271,840 B2 | 4/2019 | Sapre |
| 10,271,841 B2 | 4/2019 | Overmyer et al. |
| 10,285,694 B2 | 5/2019 | Viola et al. |
| 10,285,698 B2 | 5/2019 | Cappola et al. |
| 10,321,907 B2 | 6/2019 | Shelton, IV et al. |
| 10,327,776 B2 | 6/2019 | Harris et al. |
| 10,335,150 B2 | 7/2019 | Shelton, IV |
| 10,349,939 B2 | 7/2019 | Shelton, IV et al. |
| 10,349,941 B2 | 7/2019 | Marczyk et al. |
| 10,390,823 B2 | 8/2019 | Shelton, IV et al. |
| 10,390,825 B2 | 8/2019 | Shelton, IV et al. |
| 10,390,828 B2 | 8/2019 | Vendely et al. |
| 10,405,857 B2 | 9/2019 | Shelton |
| 10,426,468 B2 | 10/2019 | Contini et al. |
| 10,441,279 B2 | 10/2019 | Shelton, IV et al. |
| 10,456,129 B2 | 10/2019 | Shelton, IV et al. |
| 10,456,130 B2 | 10/2019 | Cheney et al. |
| 10,463,368 B2 | 11/2019 | Kostrzewski |
| 10,470,762 B2 | 11/2019 | Leimbach et al. |
| 10,470,911 B2 | 11/2019 | Thompson et al. |
| 10,478,182 B2 | 11/2019 | Taylor |
| 10,478,183 B2 | 11/2019 | Hess et al. |
| 10,478,187 B2 | 11/2019 | Shelton, IV et al. |
| 10,542,976 B2 | 1/2020 | Calderoni et al. |
| 10,548,504 B2 | 2/2020 | Shelton, IV et al. |
| 10,548,593 B2 | 2/2020 | Shelton, IV et al. |
| 10,548,599 B2 | 2/2020 | Marczyk et al. |
| 10,561,417 B2 | 2/2020 | Zergiebel et al. |
| 10,561,418 B2 | 2/2020 | Richard et al. |
| 10,568,621 B2 | 2/2020 | Shelton, IV et al. |
| 10,588,629 B2 | 3/2020 | Malinouskas et al. |
| 10,595,929 B2 | 3/2020 | Boudreaux et al. |
| 10,603,128 B2 | 3/2020 | Zergiebel et al. |
| 10,617,412 B2 | 4/2020 | Shelton, IV et al. |
| 10,624,634 B2 | 4/2020 | Shelton, IV et al. |
| 10,687,806 B2 | 6/2020 | Shelton, IV et al. |
| 10,695,053 B2 | 6/2020 | Hess et al. |
| 10,779,822 B2 | 9/2020 | Yates et al. |
| 10,792,038 B2 | 10/2020 | Becerra et al. |
| 10,828,030 B2 | 11/2020 | Weir et al. |
| 10,863,984 B2 | 12/2020 | Shelton, IV et al. |
| 2004/0108357 A1 | 6/2004 | Milliman et al. |
| 2004/0199180 A1 | 10/2004 | Knodel et al. |
| 2004/0199181 A1 | 10/2004 | Knodel et al. |
| 2004/0243151 A1 | 12/2004 | Demmy et al. |
| 2004/0267310 A1 | 12/2004 | Racenet et al. |
| 2005/0216055 A1 | 9/2005 | Scirica et al. |
| 2006/0049229 A1 | 3/2006 | Milliman et al. |
| 2006/0180634 A1 | 8/2006 | Shelton et al. |
| 2006/0289602 A1 | 12/2006 | Wales et al. |
| 2007/0073341 A1 | 3/2007 | Smith et al. |
| 2007/0084897 A1 | 4/2007 | Shelton et al. |
| 2007/0102472 A1 | 5/2007 | Shelton |
| 2007/0106317 A1 | 5/2007 | Shelton et al. |
| 2007/0119901 A1 | 5/2007 | Ehrenfels et al. |
| 2007/0145096 A1 | 6/2007 | Viola et al. |
| 2007/0170225 A1 | 7/2007 | Shelton et al. |
| 2007/0175950 A1 | 8/2007 | Shelton et al. |
| 2007/0175951 A1 | 8/2007 | Shelton et al. |
| 2007/0175955 A1 | 8/2007 | Shelton et al. |
| 2007/0194079 A1 | 8/2007 | Hueil et al. |
| 2007/0194082 A1 | 8/2007 | Morgan et al. |
| 2008/0029570 A1 | 2/2008 | Shelton et al. |
| 2008/0029573 A1 | 2/2008 | Shelton et al. |
| 2008/0029574 A1 | 2/2008 | Shelton et al. |
| 2008/0029575 A1 | 2/2008 | Shelton et al. |
| 2008/0078802 A1 | 4/2008 | Hess et al. |
| 2008/0110961 A1 | 5/2008 | Voegele et al. |
| 2008/0169328 A1 | 7/2008 | Shelton |
| 2008/0169332 A1 | 7/2008 | Shelton et al. |
| 2008/0169333 A1 | 7/2008 | Shelton et al. |
| 2008/0287987 A1 | 11/2008 | Boyden et al. |
| 2008/0296346 A1 | 12/2008 | Shelton, IV et al. |
| 2008/0308602 A1 | 12/2008 | Timm et al. |
| 2008/0308603 A1 | 12/2008 | Shelton et al. |
| 2008/0308608 A1 | 12/2008 | Prommersberger |
| 2009/0001121 A1 | 1/2009 | Hess et al. |
| 2009/0001130 A1 | 1/2009 | Hess et al. |
| 2009/0090763 A1 | 4/2009 | Zemlok et al. |
| 2009/0090766 A1 | 4/2009 | Knodel |
| 2009/0242610 A1 | 10/2009 | Shelton, IV et al. |
| 2009/0255974 A1 | 10/2009 | Viola |
| 2009/0308907 A1 | 12/2009 | Nalagatla et al. |
| 2010/0012703 A1 | 1/2010 | Calabrese et al. |
| 2010/0065604 A1 | 3/2010 | Weng |
| 2010/0069942 A1 | 3/2010 | Shelton, IV |
| 2010/0127041 A1 | 5/2010 | Morgan et al. |
| 2010/0133317 A1 | 6/2010 | Shelton, IV et al. |
| 2010/0147921 A1 | 6/2010 | Olson |
| 2010/0147922 A1 | 6/2010 | Olson |
| 2010/0155453 A1 | 6/2010 | Bombard et al. |
| 2010/0193566 A1 | 8/2010 | Scheib et al. |
| 2010/0224668 A1 | 9/2010 | Fontayne et al. |
| 2010/0249802 A1 | 9/2010 | May et al. |
| 2010/0252611 A1 | 10/2010 | Ezzat et al. |
| 2011/0006101 A1 | 1/2011 | Hall et al. |
| 2011/0024477 A1 | 2/2011 | Hall |
| 2011/0024478 A1 | 2/2011 | Shelton, IV |
| 2011/0036891 A1 | 2/2011 | Zemlok et al. |

(56) References Cited

U.S. PATENT DOCUMENTS

| | | |
|---|---|---|
| 2011/0087276 A1 | 4/2011 | Bedi et al. |
| 2011/0101069 A1 | 5/2011 | Bombard et al. |
| 2011/0147433 A1 | 6/2011 | Shelton, IV et al. |
| 2011/0163146 A1 | 7/2011 | Ortiz et al. |
| 2011/0192882 A1 | 8/2011 | Hess et al. |
| 2011/0278343 A1 | 11/2011 | Knodel et al. |
| 2011/0290856 A1 | 12/2011 | Shelton, IV et al. |
| 2012/0053406 A1 | 3/2012 | Conlon et al. |
| 2012/0061446 A1 | 3/2012 | Knodel et al. |
| 2012/0074200 A1 | 3/2012 | Schmid et al. |
| 2012/0080478 A1 | 4/2012 | Morgan et al. |
| 2012/0080495 A1 | 4/2012 | Holcomb et al. |
| 2012/0080498 A1 | 4/2012 | Shelton, IV et al. |
| 2012/0091183 A1 | 4/2012 | Manoux et al. |
| 2012/0138659 A1 | 6/2012 | Marczyk et al. |
| 2012/0193394 A1 | 8/2012 | Holcomb et al. |
| 2012/0193399 A1 | 8/2012 | Holcomb et al. |
| 2012/0211542 A1 | 8/2012 | Racenet |
| 2012/0228358 A1 | 9/2012 | Zemlok et al. |
| 2012/0234895 A1 | 9/2012 | O'Connor et al. |
| 2012/0234897 A1 | 9/2012 | Shelton, IV et al. |
| 2012/0241504 A1 | 9/2012 | Soltz et al. |
| 2012/0248169 A1 | 10/2012 | Widenhouse et al. |
| 2012/0286022 A1 | 11/2012 | Olson et al. |
| 2012/0298722 A1 | 11/2012 | Hess et al. |
| 2013/0008937 A1 | 1/2013 | Viola |
| 2013/0012983 A1 | 1/2013 | Kleyman |
| 2013/0020375 A1 | 1/2013 | Shelton, IV et al. |
| 2013/0020376 A1 | 1/2013 | Shelton, IV et al. |
| 2013/0026208 A1 | 1/2013 | Shelton, IV et al. |
| 2013/0026210 A1 | 1/2013 | Shelton, IV et al. |
| 2013/0041406 A1 | 2/2013 | Bear et al. |
| 2013/0068816 A1 | 3/2013 | Mandakolathur Vasudevan et al. |
| 2013/0068818 A1 | 3/2013 | Kasvikis |
| 2013/0075447 A1 | 3/2013 | Weisenburgh, II et al. |
| 2013/0098970 A1 | 4/2013 | Racenet et al. |
| 2013/0146642 A1* | 6/2013 | Shelton, IV ............ A61B 50/30 227/177.1 |
| 2013/0153641 A1 | 6/2013 | Shelton, IV et al. |
| 2013/0175316 A1 | 7/2013 | Thompson et al. |
| 2013/0256380 A1 | 10/2013 | Schmid et al. |
| 2013/0277410 A1 | 10/2013 | Fernandez et al. |
| 2013/0334280 A1 | 12/2013 | Krehel et al. |
| 2013/0334287 A1* | 12/2013 | Shelton, IV ....... A61B 17/1155 227/180.1 |
| 2014/0014704 A1 | 1/2014 | Onukuri et al. |
| 2014/0014707 A1 | 1/2014 | Onukuri et al. |
| 2014/0048580 A1* | 2/2014 | Merchant ......... A61B 17/07292 227/176.1 |
| 2014/0166724 A1 | 6/2014 | Schellin et al. |
| 2014/0166725 A1 | 6/2014 | Schellin et al. |
| 2014/0166726 A1 | 6/2014 | Schellin et al. |
| 2014/0175150 A1 | 6/2014 | Shelton, IV et al. |
| 2014/0239047 A1* | 8/2014 | Hodgkinson .... A61B 17/07207 227/180.1 |
| 2014/0246475 A1 | 9/2014 | Hall et al. |
| 2014/0252064 A1 | 9/2014 | Mozdzierz et al. |
| 2014/0263541 A1 | 9/2014 | Leimbach et al. |
| 2014/0263552 A1 | 9/2014 | Hall et al. |
| 2014/0263558 A1 | 9/2014 | Hausen et al. |
| 2014/0284371 A1 | 9/2014 | Morgan et al. |
| 2014/0291379 A1 | 10/2014 | Schellin et al. |
| 2014/0291383 A1 | 10/2014 | Spivey et al. |
| 2014/0367445 A1 | 12/2014 | Ingmanson et al. |
| 2015/0076211 A1 | 3/2015 | Irka et al. |
| 2015/0129634 A1* | 5/2015 | Shelton, IV ..... A61B 17/07292 227/176.1 |
| 2015/0134076 A1 | 5/2015 | Shelton, IV et al. |
| 2015/0173749 A1 | 6/2015 | Shelton, IV et al. |
| 2015/0173756 A1 | 6/2015 | Baxter, III et al. |
| 2015/0250474 A1 | 9/2015 | Abbott et al. |
| 2015/0272557 A1 | 10/2015 | Overmyer et al. |
| 2015/0297222 A1 | 10/2015 | Huitema et al. |
| 2015/0297225 A1* | 10/2015 | Huitema ............. A61B 17/105 227/176.1 |
| 2015/0374372 A1 | 12/2015 | Zergiebel et al. |
| 2016/0066909 A1 | 3/2016 | Baber et al. |
| 2016/0166249 A1 | 6/2016 | Knodel |
| 2016/0166253 A1 | 6/2016 | Knodel |
| 2016/0235494 A1 | 8/2016 | Shelton, IV et al. |
| 2016/0302791 A1 | 10/2016 | Schmitt |
| 2016/0354176 A1 | 12/2016 | Schmitt |
| 2017/0000483 A1 | 1/2017 | Motai et al. |
| 2017/0086838 A1* | 3/2017 | Harris ................. A61B 17/105 |
| 2017/0112561 A1 | 4/2017 | Motai |
| 2017/0290584 A1 | 10/2017 | Jasemian et al. |
| 2017/0296172 A1 | 10/2017 | Harris et al. |
| 2017/0303924 A1 | 10/2017 | Scheib |
| 2018/0008260 A1 | 1/2018 | Baxter, III et al. |
| 2018/0116658 A1* | 5/2018 | Aronhalt, IV ....... A61B 17/072 |
| 2018/0168637 A1 | 6/2018 | Harris |
| 2018/0168644 A1 | 6/2018 | Shelton, IV et al. |
| 2018/0235610 A1 | 8/2018 | Harris et al. |
| 2018/0325514 A1 | 11/2018 | Harris et al. |
| 2018/0353180 A1* | 12/2018 | Huitema ......... A61B 17/07207 |
| 2018/0353659 A1* | 12/2018 | Widenhouse .... A61B 17/07207 |
| 2019/0099181 A1 | 4/2019 | Shelton, IV et al. |
| 2019/0099182 A1 | 4/2019 | Bakos et al. |
| 2019/0150919 A1 | 5/2019 | Williams et al. |
| 2019/0175173 A1 | 6/2019 | Harris et al. |
| 2019/0261984 A1 | 8/2019 | Nelson et al. |
| 2019/0298341 A1 | 10/2019 | Shelton, IV et al. |
| 2019/0314016 A1 | 10/2019 | Huitema et al. |
| 2019/0314019 A1 | 10/2019 | Rector et al. |
| 2020/0054323 A1 | 2/2020 | Harris et al. |
| 2020/0121317 A1 | 4/2020 | Kostrzewski |
| 2020/0237368 A1 | 7/2020 | Bruns et al. |
| 2020/0281587 A1* | 9/2020 | Schmid ............ A61B 17/07292 |
| 2021/0077102 A1 | 3/2021 | Williams |

FOREIGN PATENT DOCUMENTS

| | | |
|---|---|---|
| CA | 2884962 A1 | 11/2015 |
| CA | 3012790 A1 * | 2/2019 ........... A61B 17/064 |
| CN | 101292888 A | 10/2008 |
| CN | 103610481 A | 3/2014 |
| CN | 106456164 A | 2/2017 |
| CN | 110099619 A | 8/2019 |
| DE | 2744824 A1 | 4/1978 |
| DE | 2903159 A1 | 7/1980 |
| DE | 3114135 A1 | 10/1982 |
| DE | 4213426 A1 | 10/1992 |
| DE | 4300307 A1 | 7/1994 |
| EP | 0041022 A1 | 12/1981 |
| EP | 0136950 A2 | 4/1985 |
| EP | 0140552 A2 | 5/1985 |
| EP | 0156774 A2 | 10/1985 |
| EP | 0213817 A1 | 3/1987 |
| EP | 0216532 A1 | 4/1987 |
| EP | 0220029 A1 | 4/1987 |
| EP | 0273468 A2 | 7/1988 |
| EP | 0324166 A2 | 7/1989 |
| EP | 0324635 A1 | 7/1989 |
| EP | 0324637 A1 | 7/1989 |
| EP | 0324638 A1 | 7/1989 |
| EP | 0365153 A1 | 4/1990 |
| EP | 0369324 A1 | 5/1990 |
| EP | 0373762 A1 | 6/1990 |
| EP | 0380025 A2 | 8/1990 |
| EP | 0399701 A1 | 11/1990 |
| EP | 0449394 A2 | 10/1991 |
| EP | 0484677 A1 | 5/1992 |
| EP | 0489436 A1 | 6/1992 |
| EP | 0503662 A1 | 9/1992 |
| EP | 0514139 A2 | 11/1992 |
| EP | 0536903 A2 | 4/1993 |
| EP | 0537572 A2 | 4/1993 |
| EP | 0539762 A1 | 5/1993 |
| EP | 0541950 A1 | 5/1993 |
| EP | 0545029 A1 | 6/1993 |
| EP | 0552050 A2 | 7/1993 |
| EP | 0552423 A2 | 7/1993 |

(56) References Cited

FOREIGN PATENT DOCUMENTS

| | | |
|---|---|---|
| EP | 0579038 A1 | 1/1994 |
| EP | 0589306 A2 | 3/1994 |
| EP | 0591946 A1 | 4/1994 |
| EP | 0592243 A2 | 4/1994 |
| EP | 0593920 A1 | 4/1994 |
| EP | 0598202 A1 | 5/1994 |
| EP | 0598579 A1 | 5/1994 |
| EP | 0600182 A2 | 6/1994 |
| EP | 0621006 A1 | 10/1994 |
| EP | 0621009 A1 | 10/1994 |
| EP | 0656188 A2 | 6/1995 |
| EP | 0666057 A2 | 8/1995 |
| EP | 0705571 A1 | 4/1996 |
| EP | 0760230 A1 | 3/1997 |
| EP | 1952769 A2 | 8/2008 |
| EP | 2090253 A2 | 8/2009 |
| EP | 2090254 A1 | 8/2009 |
| EP | 2583630 A2 | 4/2013 |
| EP | 2586382 A2 | 5/2013 |
| EP | 2907456 A1 | 8/2015 |
| EP | 3138509 A1 | 3/2017 |
| EP | 3162305 A1 * 5/2017 ....... A61B 17/00234 |
| EP | 3235450 A1 * 10/2017 ........... A61B 17/068 |
| EP | 3338660 A1 | 6/2018 |
| FR | 391239 A | 10/1908 |
| FR | 2542188 A1 | 9/1984 |
| FR | 2660851 A1 | 10/1991 |
| FR | 2681775 A1 | 4/1993 |
| GB | 1352554 A | 5/1974 |
| GB | 1452185 A | 10/1976 |
| GB | 1555455 A | 11/1979 |
| GB | 2048685 A | 12/1980 |
| GB | 2070499 A | 9/1981 |
| GB | 2141066 A | 12/1984 |
| GB | 2165559 A | 4/1986 |
| JP | 51149985 | 12/1976 |
| JP | 2001087272 | 4/2001 |
| JP | 2013215572 A | 10/2013 |
| SU | 659146 A1 | 4/1979 |
| SU | 728848 A1 | 4/1980 |
| SU | 980703 A1 | 12/1982 |
| SU | 990220 A1 | 1/1983 |
| WO | 2008302247 | 7/1983 |
| WO | 8910094 A1 | 11/1989 |
| WO | 9210976 A1 | 7/1992 |
| WO | 9308754 A1 | 5/1993 |
| WO | 9314706 A1 | 8/1993 |
| WO | 2004032760 A2 | 4/2004 |
| WO | 2009071070 A2 | 6/2009 |
| WO | 2015191887 A1 | 12/2015 |
| WO | 2018161313 A1 | 9/2018 |
| WO | 2019116272 A1 | 6/2019 |
| WO | 2019186434 A1 | 10/2019 |

OTHER PUBLICATIONS

International Search Report and Written Opinion dated Oct. 26, 2020, issued in corresponding international appln. No. PCT/CN2020/074186, 7 pages.

European Search Report dated Sep. 5, 2023, issued in corresponding EP Appln. No. 20917726, 9 pages.

* cited by examiner

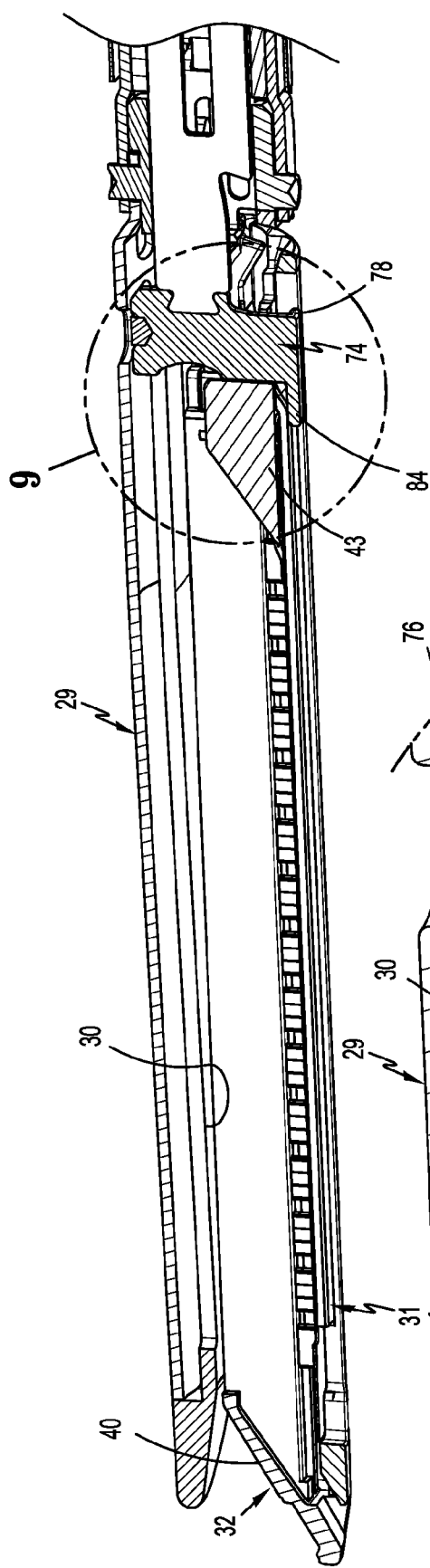
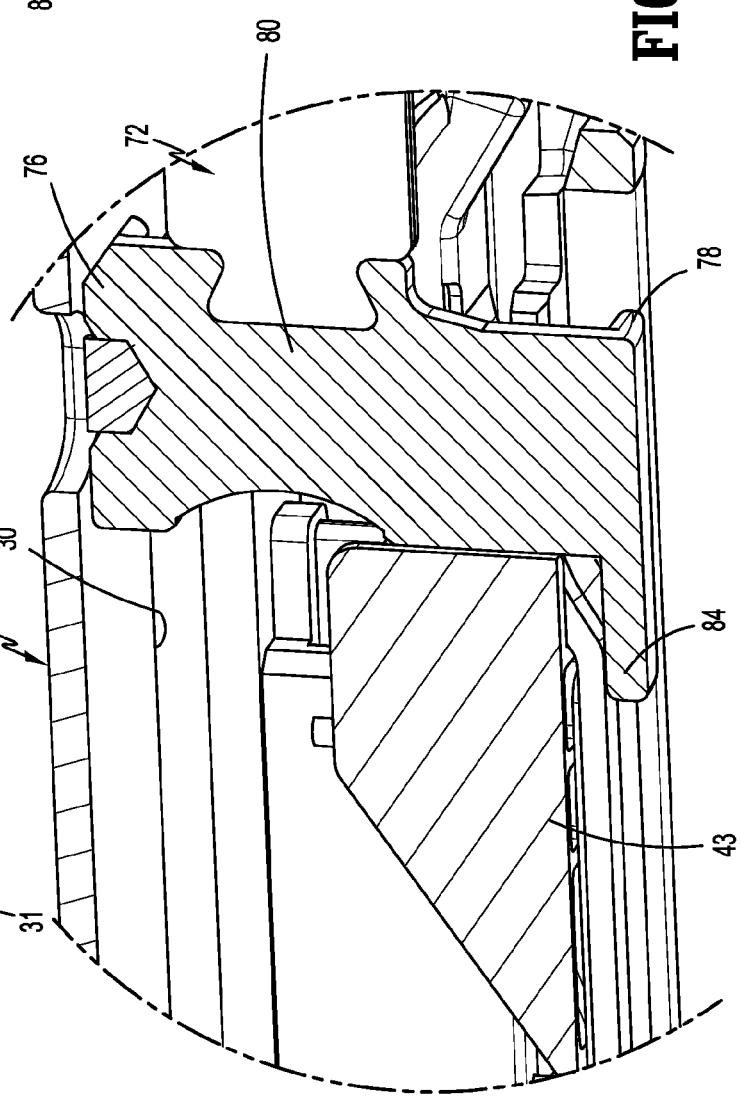

SURGICAL STAPLING DEVICE

FIELD

This technology is generally related to surgical stapling devices and, more particularly, to surgical stapling devices for endoscopic use.

BACKGROUND

Surgical stapling devices for endoscopic use are well known and commonly used to minimize patient trauma and reduce patient recovery times. Typically, endoscopic stapling devices include a linear tool assembly that has an anvil assembly and a cartridge assembly that are coupled to each other by a pivot member and movable in relation to each other between open and clamped positions. In the clamped position, the stapling device defines a tissue gap between the anvil assembly and the cartridge assembly to receive tissue to be treated.

In use, the tool assembly of an endoscopic stapling device is inserted through a small incision in the skin or through a small diameter cannula. In order to introduce the tool assembly through a cannula having the smallest diameter, the tool assembly is inserted through the cannula in its clamped position. If the tool assembly does not move to a fully clamped position, the tool assembly will not be able to enter the cannula.

A continuing need exists in the art for an endoscopic surgical stapling device including a tool assembly that moves to its fully clamped position when the tool assembly is clamped to facilitate insertion of the tool assembly through a cannula.

SUMMARY

In aspects, this disclosure generally relates to a stapling device that includes a tool assembly and a drive assembly having a clamp member that supports a distal extension. The clamp member is movable from a retracted position to a partially advanced position to move the tool assembly from an open position to a clamped position to define a tissue gap within the tool assembly. The distal extension is positioned distally of the clamp member and engages the tool assembly to urge the tool assembly to an insertion position in which the tool assembly no longer defines a tissue gap.

One aspect of the disclosure is directed to a stapling device including an elongate body, a tool assembly, and a drive assembly. The elongate body has a proximal end portion secured to the handle assembly and a distal end portion. The tool assembly is supported on the distal end portion of the elongate body and includes an anvil and a cartridge assembly. The cartridge assembly is movable in relation to the anvil from between an open position to a clamped position in which the cartridge assembly and the anvil define a predetermined tissue gap. The cartridge assembly includes a cartridge channel and a staple cartridge. The cartridge channel includes an outer surface defining a ramp. The drive assembly includes a drive beam a distal end portion and a damp member. The clamp member is supported on the distal end portion of the drive beam and includes a first beam, a second beam, and a vertical strut interconnecting the first beam and the second beam. The drive assembly is movable between a retracted position and a partially advanced position to move the first and second beams into the ramp to move the tool assembly from the open position to the clamped position. The drive assembly is movable from the partially advanced position to a fully advanced position to actuate the tool assembly. The first beam of the clamp member engages the anvil and the second beam of the clamp member engages the cartridge channel of the cartridge assembly. The second beam supports a distal extension that extends distally of the first beam and the second beam. The distal extension engages the outer surface of the cartridge channel distally of the ramp when the drive assembly is in the partially advanced position to move the tool assembly to an insertion position in which a distal end portion of the staple cartridge is engaged with the anvil.

In aspects of the disclosure, the outer surface of the cartridge channel includes dimples positioned distally of the ramp, and the distal extension of the second beam engages the dimples when the drive assembly is in the partially advanced position.

In some aspects of the disclosure, the dimples are supported on cantilevered portions of the cartridge channel, wherein the cantilevered portions allow the flexible dimples to flex out of the path of the second beam when the drive assembly is moved to the advanced position.

In certain aspects of the disclosure, the distal extension extends distally of the first and second beams a distance "X", wherein "X" is from about 0.1 inches and to about 0.25 inches.

In aspects of the disclosure, the distal extension has a width and the second beam has a width, and the width of the distal extension is smaller than the width of the second beam.

In some aspects of the disclosure, the stapling device includes a rotation knob that is rotatably coupled to the handle assembly and supports the elongate body such that rotation of the rotation knob in relation to the handle assembly effects rotation of the elongate body and the tool assembly in relation to the handle assembly.

In certain aspects of the disclosure, the stapling device includes a handle assembly having a stationary handle and a trigger.

Other aspects of this disclosure are directed to a tool assembly including an anvil, a cartridge assembly, and a drive assembly. The cartridge assembly is movable in relation to the anvil from an open position to a clamped position in which the cartridge assembly and the anvil define a predetermined maximum tissue gap. The cartridge assembly includes a cartridge channel and a staple cartridge. The cartridge channel includes an outer surface defining a ramp. The drive assembly includes a drive beam having a distal end portion and a clamp member. The clamp member is supported on the distal end portion of the drive beam and includes a first beam, a second beam, and a vertical strut interconnecting the first beam and the second beam. The drive assembly is movable between a retracted position and a partially advanced position to move the tool assembly from the open position to the clamped position, and movable from the partially advanced position to a fully advanced position to actuate the tool assembly. The first beam engages the anvil and the second beam engages the cartridge channel of the cartridge assembly. The second beam includes a distal extension that extends distally of the first beam. The distal extension engages the outer surface of the cartridge channel distally of the ramp when the drive assembly is in the partially advanced position to move the tool assembly to an insertion position in which the staple cartridge is engaged with the anvil.

Other aspects of this disclosure are directed to a tool assembly including an anvil, a cartridge assembly, and a drive assembly. The cartridge assembly is movable in relation to the anvil from an open position to a clamped position in which the cartridge assembly and the anvil define a predetermined maximum tissue gap. The cartridge assembly includes a cartridge channel and a staple cartridge. The cartridge channel has an outer surface defining a ramp. The drive assembly includes a drive beam having a distal end portion and a clamp member. The clamp member is supported on the distal end portion of the drive beam and includes a first beam, a second beam having a first width, and a vertical strut interconnecting the first beam and the second beam. The drive assembly is movable between a retracted position and a partially advanced position to move the tool assembly from the open position to the clamped position, and movable from the partially advanced position to a fully advanced position to actuate the tool assembly. The first beam engages the anvil and the second beam engages the cartridge channel of the cartridge assembly. The second beam includes a distal extension that extends distally of the first beam. The distal extension has a second width smaller than the first width of the second beam. The distal extension engages the outer surface of the cartridge channel distally of the ramp when the drive assembly is in the partially advanced position to move the tool assembly to an insertion position in which the staple cartridge is engaged with the anvil. The outer surface of the cartridge channel includes dimples positioned distally of the ramp. The distal extension of the second beam engages the dimples when the drive assembly is in the partially advanced position.

Other features of the disclosure will be appreciated from the following description.

BRIEF DESCRIPTION OF DRAWINGS

Various aspects of the disclosure are described herein below with reference to the drawings, wherein:

FIG. 2A is a side perspective view of the cartridge channel of the surgical stapling device shown in FIG. 1;

FIG. 8 is a cross-sectional view taken along section line 8-8 of FIG. 6;

FIG. 9 an enlarged view of the indicated area of detail shown in FIG. 8;

DETAILED DESCRIPTION

Figure 1:
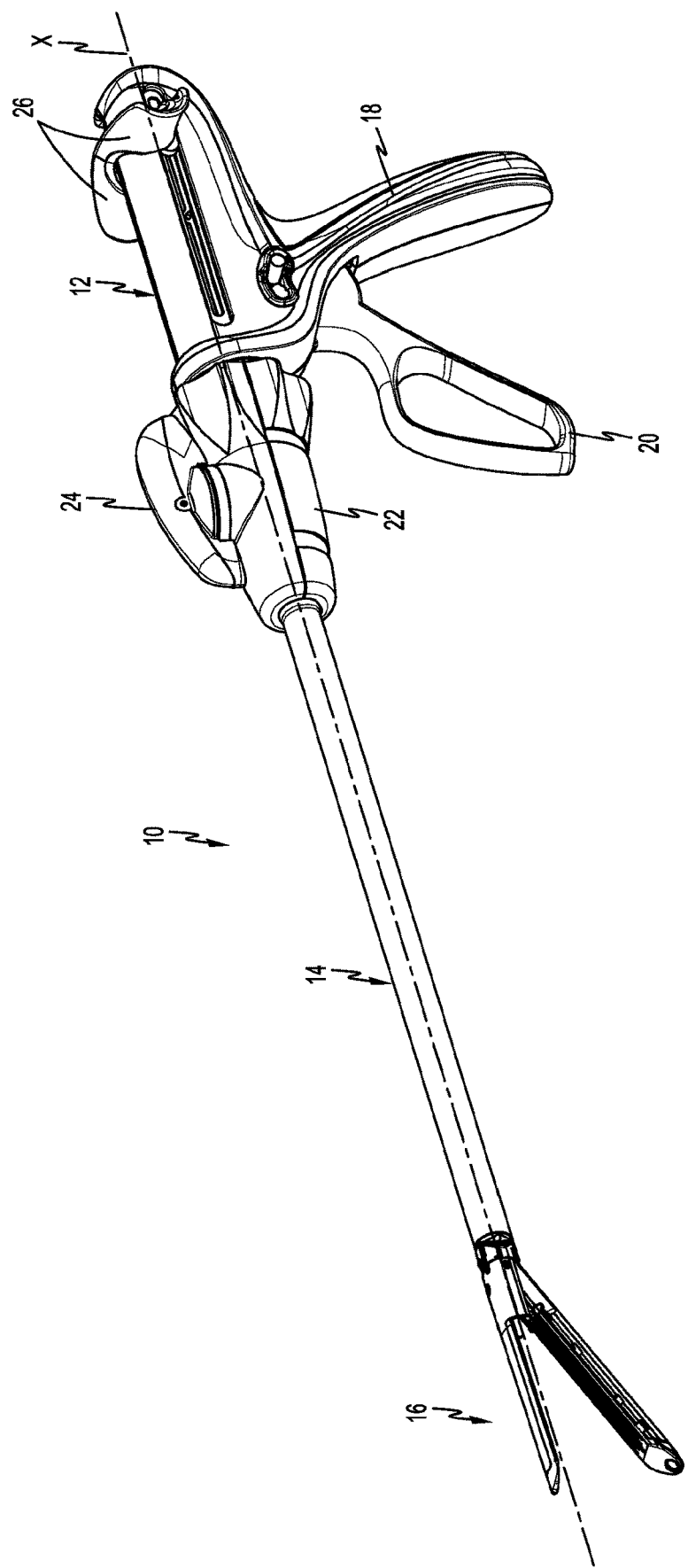
FIG. 1 is a perspective view of exemplary aspects of the disclosed surgical stapling device including a tool assembly in an open position.

The disclosed surgical stapling device will now be described in detail with reference to the drawings in which like reference numerals designate identical or corresponding elements in each of the several views. However, it is to be understood that the aspects of the disclosure are merely exemplary of the disclosure and may be embodied in various forms. Well-known functions or constructions are not described in detail to avoid obscuring the disclosure in unnecessary detail. Therefore, specific structural and functional details disclosed herein are not to be interpreted as limiting, but merely as a basis for the claims and as a representative basis for teaching one skilled in the art to variously employ the disclosure in virtually any appropriately detailed structure. In addition, directional terms such as front, rear, upper, lower, top, bottom, distal, proximal, and similar terms are used to assist in understanding the description and are not intended to limit the disclosure.

In this description, the term "proximal" is used generally to refer to that portion of the device that is closer to a clinician, while the term "distal" is used generally to refer to that portion of the device that is farther from the clinician. In addition, the term "endoscopic" is used generally used to refer to endoscopic, laparoscopic, arthroscopic, and/or any other procedure conducted through a small diameter incision or cannula. Further, the term "clinician" is used generally to refer to medical personnel including doctors, nurses, and support personnel.

The disclosed surgical stapling device includes a tool assembly having a pair of jaws supporting a cartridge assembly and an anvil assembly. The jaws are pivotably coupled to each other and are movable in relation to each other between open and clamped positions. The stapling device includes a drive assembly having a clamping member that is movable through the tool assembly to eject staples from the cartridge assembly into the anvil assembly and to dissect tissue. The clamp member includes first and second beams that are vertically aligned and engage the anvil and cartridge assemblies to move the anvil and cartridge assemblies between the open and clamped positions. In the clamped position, the anvil and cartridge assemblies define a maximum tissue gap. The clamp member includes an extension that extends distally of the first and second beams and engages one of the jaws to urge the distal end of the cartridge assembly or anvil assembly supported on the engaged jaw to an insertion position engaged with the other of the cartridge assembly or anvil assembly supported on the other jaw to minimize the diameter of the tool assembly at a distal end of the tool assembly.

FIG. 1 illustrates exemplary aspects of the disclosed surgical stapling device shown generally as stapling device 10. The stapling device 10 includes a handle assembly 12, an elongate body 14 defining a longitudinal axis "X", and a tool assembly 16. The handle assembly 12 includes a stationary handle 18 and a trigger 20 that is movable in relation to the stationary handle 18 to actuate the tool assembly 16. In aspects of the disclosure, the stapling device 10 includes a rotation knob 22 and an articulation lever 24. The rotation knob 22 is coupled to the handle assembly 12 and to the elongate body 14 to facilitate rotation of the elongate body 14 and tool assembly 16 in relation to the handle assembly 12 about the longitudinal axis "X". The articulation lever 24 is coupled to the tool assembly 16 to articulate the tool assembly 16 from a position aligned with the longitudinal axis "X" to positions defining acute angles with the longitudinal axis "X". In some aspects of the stapling device 10, the handle assembly 12 includes retraction knobs 26 for retracting a drive assembly of the stapling device 10. For a more detailed description of exemplary aspects of the handle assembly 12 of the stapling device 10, see, e.g., U.S. Pat. No. 6,241,139 ("the '139 patent"). Although the handle assembly 12 is illustrated as a manually operated handle assembly, it is envisioned that the handle assembly 12 could be a powered handle assembly such as described in U.S. Pat. No. 9,055,943.

Figure 2:
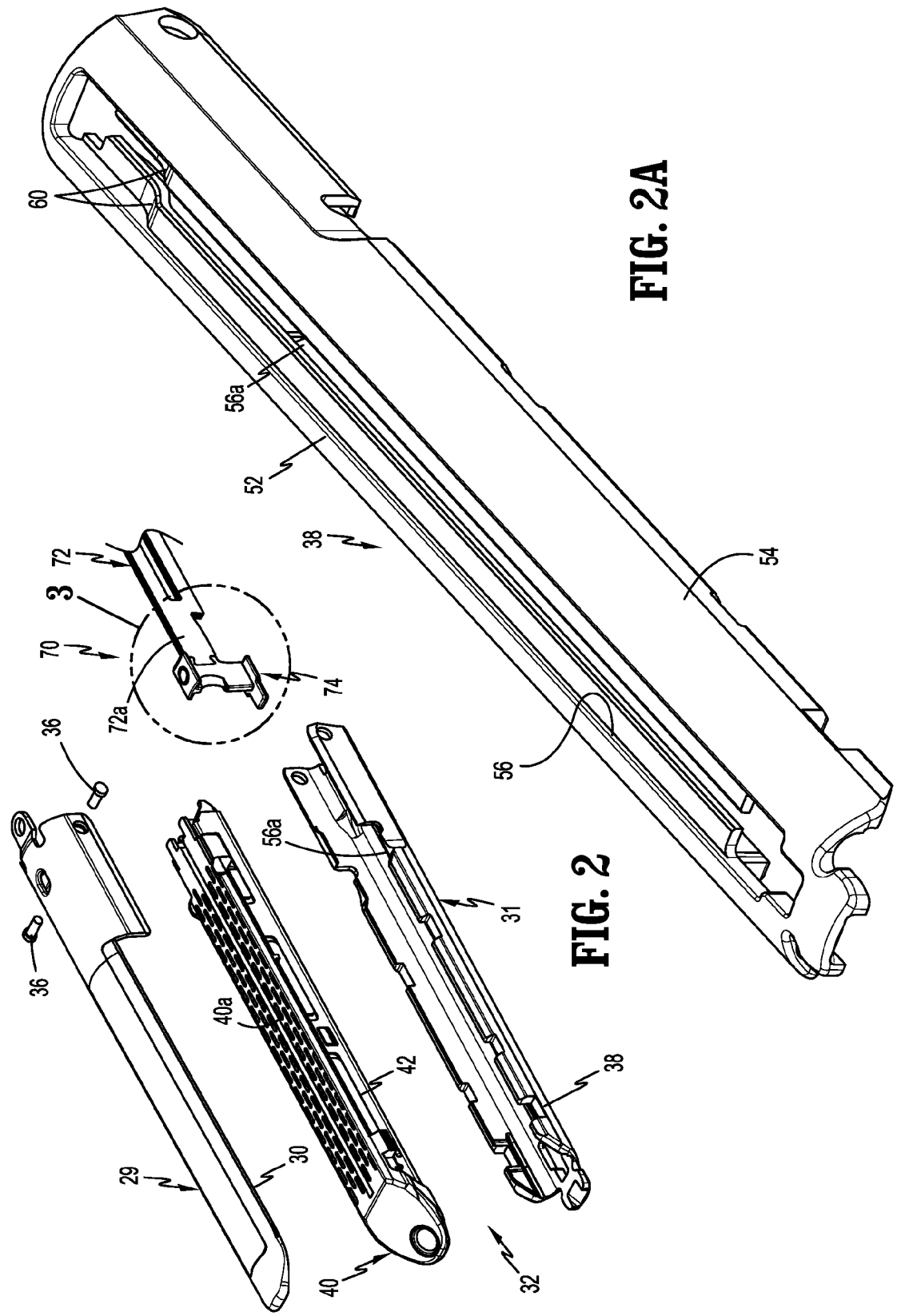
FIG. 2 is an exploded, side perspective view of the tool assembly of the stapling device shown in FIG. 1.

FIG. 2 illustrates the tool assembly 16 of the stapling device 10 (FIG. 1) which includes a first jaw 29 supporting an anvil 30 and a second jaw 31 supporting a cartridge assembly 32. The first and second jaws 29, 31 are coupled together with pivot members 36 such that the cartridge assembly 32 can pivot in relation to the anvil 30 between an open position (FIG. 1) and a clamped position (FIG. 8). Although the cartridge assembly 32 is illustrated as pivoting towards a stationary anvil 30, it is envisioned that the anvil 30 could pivot towards a stationary cartridge assembly 32.

The cartridge assembly 32 includes a cartridge channel 38 and a staple cartridge 40. The staple cartridge 40 includes a cartridge body 42 that defines a knife slot 40a and supports an actuation sled 43 (FIG. 9), a plurality of staples (not shown), and pushers (not shown). For a detailed description of an exemplary staple cartridge, see, e.g., the '139 patent.

FIG. 2A illustrates the cartridge channel 38 which includes a body 50 having an outer wall 52 and spaced side walls 54. The outer wall 52 defines an elongate recess 56 and an elongate slot 56a that extends within the recess 56 from a position adjacent a distal end of the cartridge channel 38 to a position adjacent the proximal end of the cartridge channel 38. The recess 56 includes a ramp 60 that is positioned on opposite sides of the elongate slot 56 adjacent the proximal end of the cartridge channel 38. The body 50 of the cartridge channel 38 is configured to releasably receive the staple cartridge 40. Upon firing of the stapling device 10, a spent or used staple cartridge 40 can be removed from the cartridge channel 38 and replaced with a fresh or new staple cartridge 40 to facilitate reuse of the stapling device 10.

Figure 3:
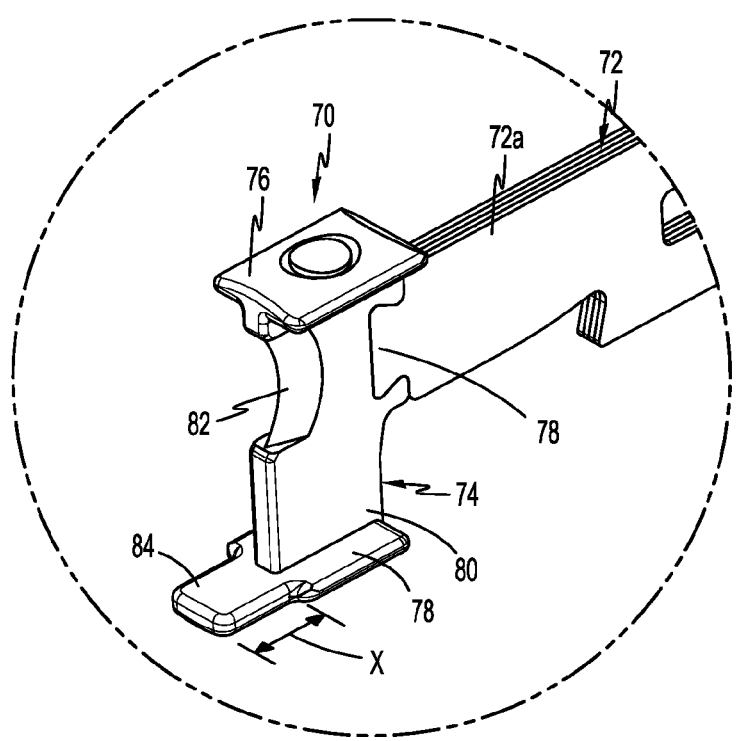
FIG. 3 is an enlarged view of the indicated area of detail shown in FIG. 2.

FIGS. 2 and 3 illustrate a drive assembly 70 of the stapling device 10. The drive assembly 70 includes a drive beam 72 and a clamp member 74 that is secured to a distal end portion 72a of the drive beam 72. In certain aspects of the disclosure, the drive beam 72 is formed from stacked sheets of a flexible material, e.g., stainless steel, and the clamp member 74 is coupled to the drive beam 72 using a dove-tail type connection 78 (FIG. 3). The clamp member 74 includes a first beam 76, a second beam 78 and a vertical strut 80 that interconnects the first beam 76 and the second beam 78. The first beam 76 is vertically aligned with second beam 78 and is engaged with the anvil 30. The second beam 78 is received within the elongate recess 56 of the cartridge channel 38. The vertical strut 80 extends through the knife slot 40a in the staple cartridge 40 and through the slot 56a in the cartridge channel 38. The drive assembly 70 is movable along the tool assembly 16 from a retracted position to an advanced position to move the tool assembly from its open position to its clamped position and to subsequently eject staples (not shown) from the staple cartridge 40. In the clamped position, the clamp member 74 is configured to define a predetermined tissue gap "G" between the anvil 30 and the staple cartridge 40. In some aspects of the disclosure, the vertical strut 80 supports a knife blade 82 that is aligned with the tissue gap defined between the anvil 30 and the staple cartridge 40 to cut tissue clamped between the anvil 30 and the staple cartridge 40.

As described above, the first beam 76 and the second beam 78 of the clamp member are in substantial vertical alignment. More specifically, the first beam 76 is positioned above the second beam 78 and is spaced from the second beam 78 by the vertical strut 80 such that a distal end of the first 76 is in substantial vertical alignment with the distal end of the second beam 78.

In aspects of the disclosure, the second beam 78 supports an extension 84 that is secured to the distal end of the second beam 78 and extends distally from the distal end of the second beam 78 a distance "X", wherein "X" is from about 0.1 inches to about 0.25 inches. (FIG. 3). In some aspects of the disclosure, the extension 84 is integrally or monolithically formed with the second beam 78.

Figure 4:
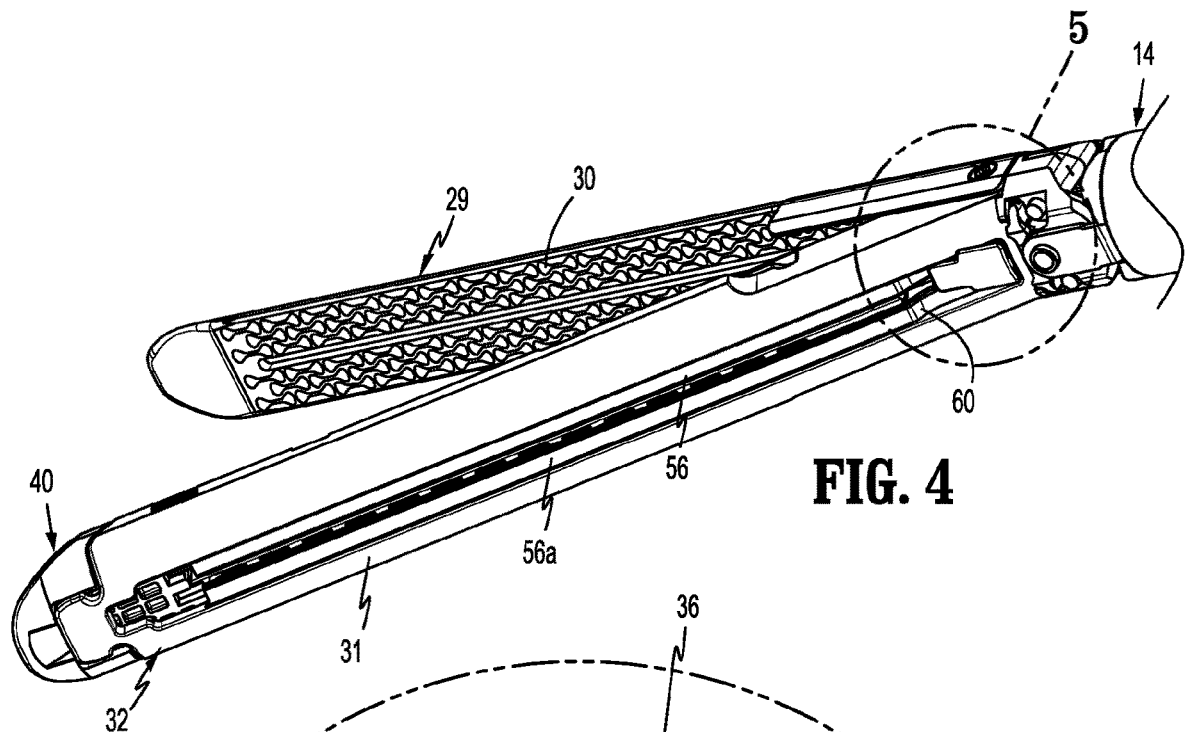
FIG. 4 is an enlarged perspective view of the tool assembly of the surgical stapling device shown in FIG. 1 in the open position.
Figure 5:
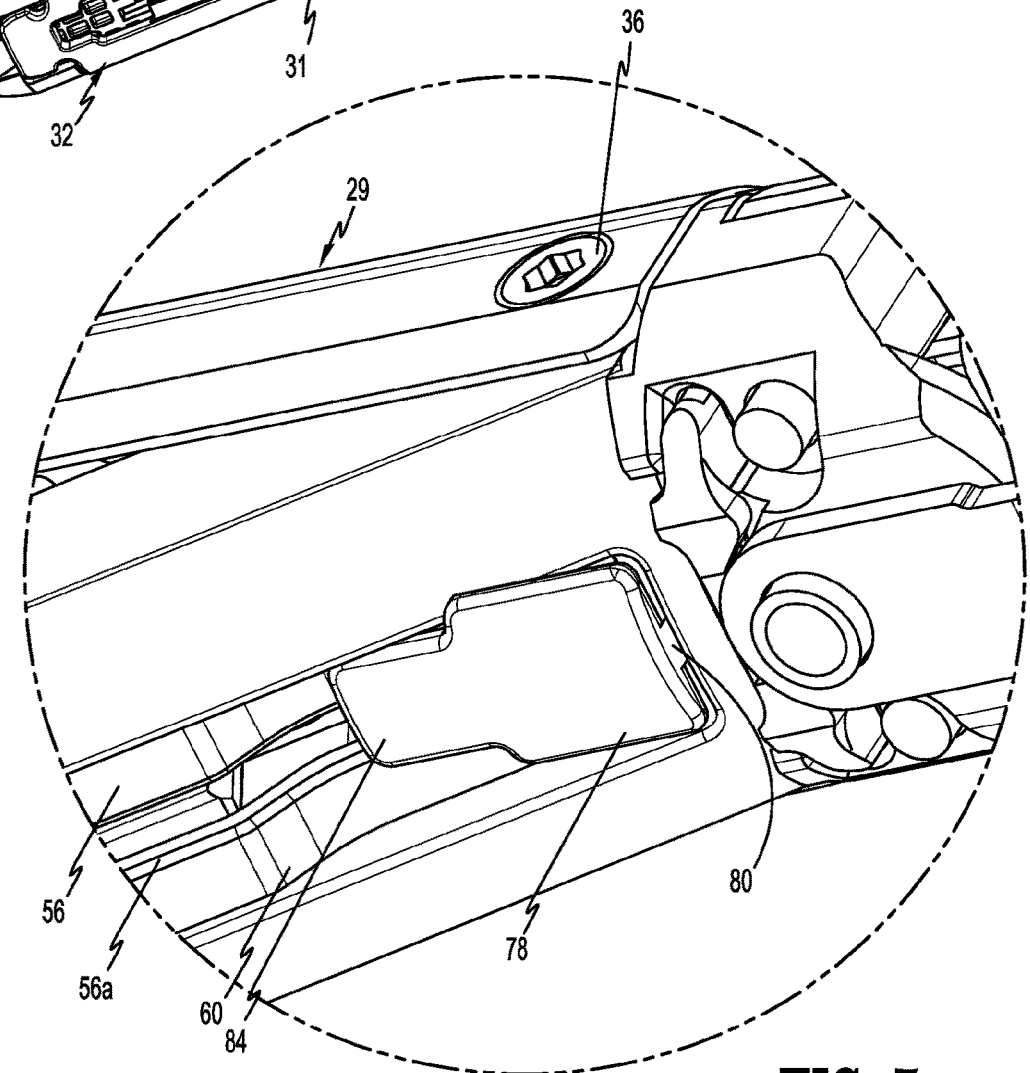
FIG. 5 is an enlarged view of the indicated area of detail shown in FIG. 4.
Figure 6:
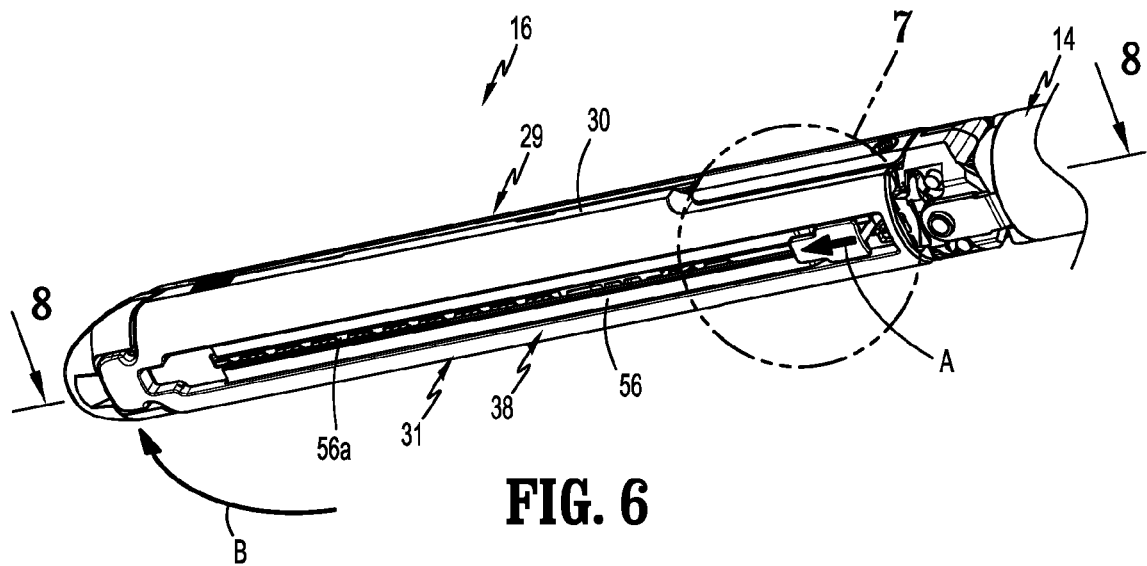
FIG. 6 is an enlarged perspective view of the tool assembly of the surgical stapling device shown in FIG. 1 in the clamped position.
Figure 7:
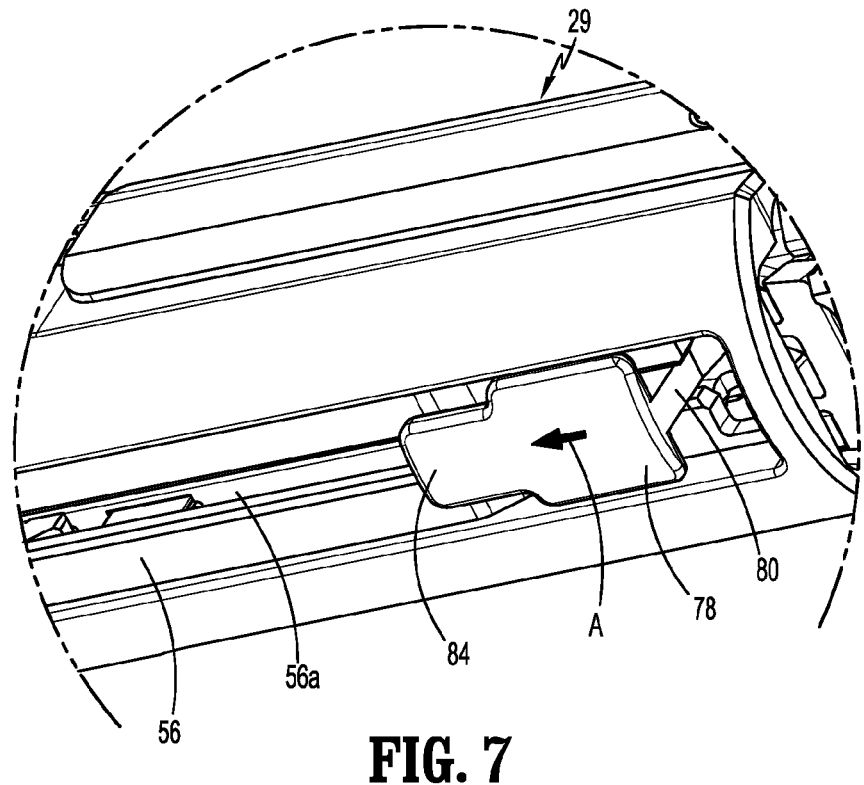
FIG. 7 is an enlarged view of the indicated area of detail shown in FIG. 6.
Figure 10:
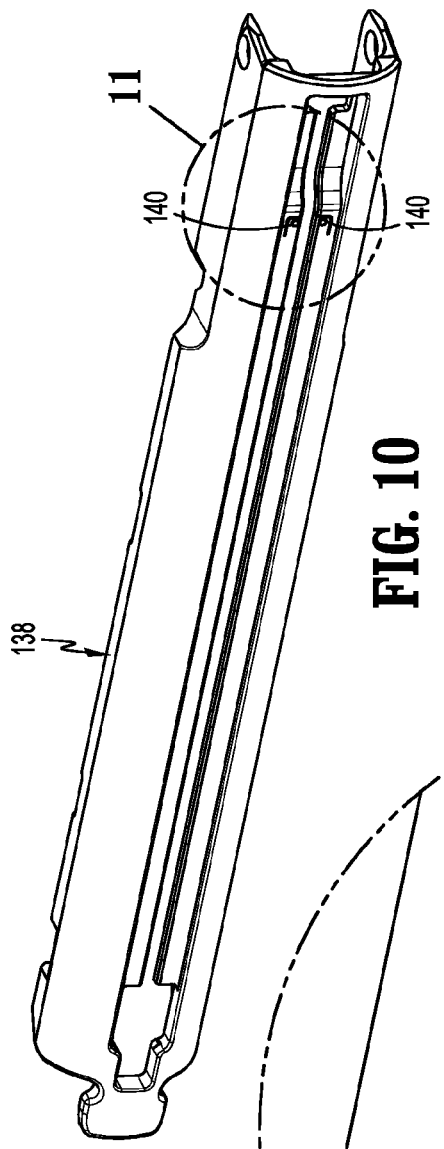
FIG. 10 is a side perspective view of an alternative cartridge channel of disclosed surgical stapling device illustrating other aspects of the disclosure.
Figure 11:
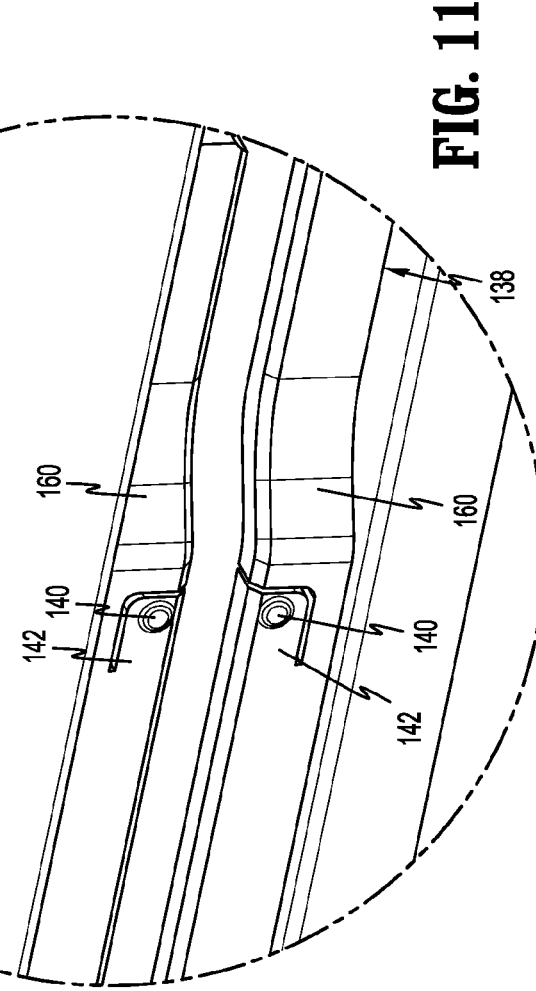
FIG. 11 is an enlarged view of the indicated area of detail shown in FIG. 10.
Figure 12:
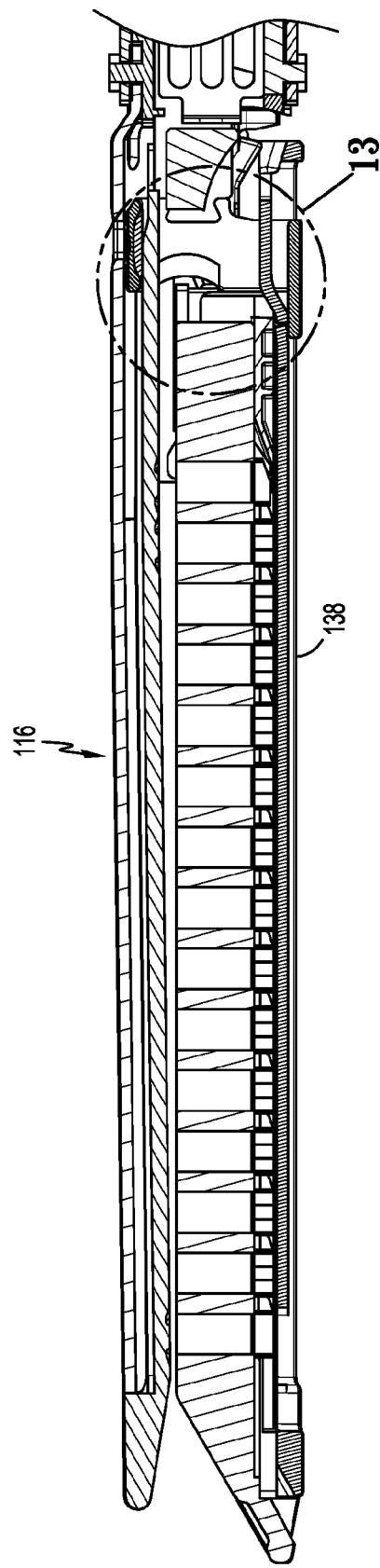
FIG. 12 is a side cross-sectional view of the tool assembly of the surgical stapling device shown in FIG. 1 with the cartridge channel shown in FIG. 11 with the tool assembly in the clamped position.
Figure 13:
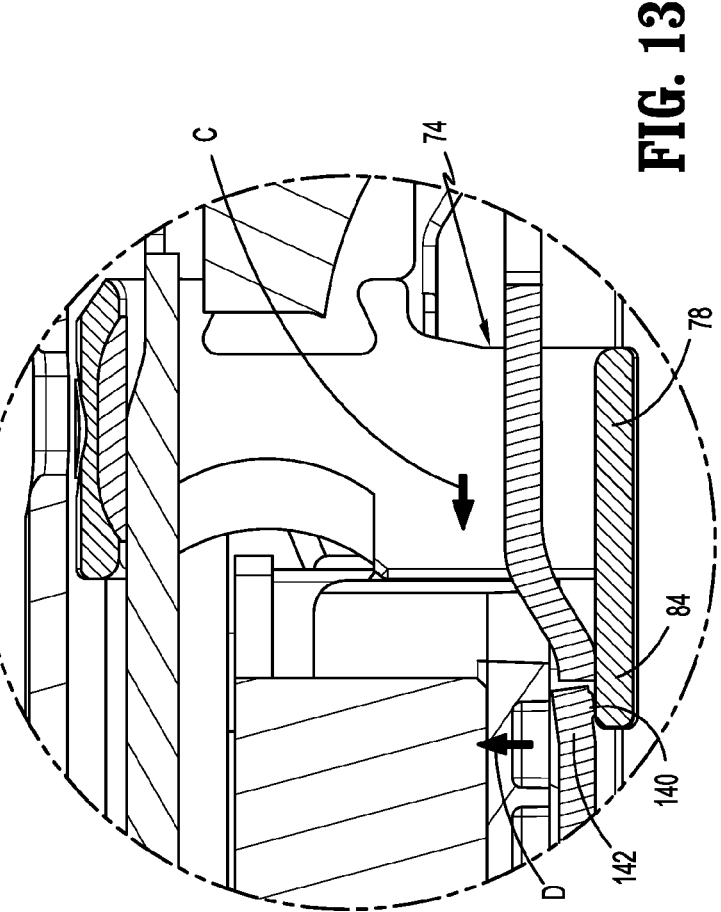
FIG. 13 is an enlarged view of the indicated area of detail shown in FIG. 12.

FIGS. 4 and 5 illustrate the tool assembly 16 in the open position with the drive assembly 70 (FIG. 2) in the retracted position. In the retracted position, the first and second beams 76, 78 and the distal extension 84 of the clamp member 74 of the drive assembly 70 are positioned proximally of the ramp 60 of the cartridge channel 38. In this position, the cartridge assembly 32 is pivoted outwardly of the anvil 30.

FIGS. 6-9 illustrate the tool assembly 16 in the clamped position with the drive assembly 70 (FIG. 2) advanced in the direction of arrow "A" to a partially advanced position. In the clamped position, the second beam 78 of the clamp member 74 is engaged with the ramp 60 on the cartridge channel 38 and the first beam 76 is engaged with the anvil first jaw 29 supporting the anvil 30. In addition, the extension 84 on the second beam 78 extends distally of the ramp 60 and is engaged with an outer surface of the cartridge channel 38 within the recess 56. When the second beam 78 of the clamp member 74 engages and moves along the ramp 60, the cartridge channel 38 and the staple cartridge 40 supported within the cartridge channel 38 are pivoted in the direction of arrow "B" in FIG. 6 to move the tool assembly 16 from the open position (FIG. 4) to the clamped position. The extension 84 on the second beam 78 extends forward of the ramp 60 and engages the cartridge channel 38 to urge the cartridge channel 38 towards the anvil 30 to an insertion position (FIG. 8) in which the staple cartridge 40 engages the anvil 30 to close the tissue gap "G" defined between the staple cartridge 40 and the anvil 30 and/or, to at least maintain the cartridge channel 38 in a position spaced from the anvil 30 a distance no greater than the predetermined tissue gap "G", i.e, the extension 84 prevents outward deflection of the cartridge channel 38 that would allow the tissue gap "G' to exceed the predetermined tissue gap "G". I This is especially important in stapling devices used for multiple firings wherein outward deflection of the cartridge channel 38 may occur due to the prior use on thick tissue. In aspects of the disclosure, the distal extension 84 has a width that is less than the width of the second beam 78.

FIGS. 10-13 illustrate a tool assembly 116 including an alternative cartridge channel shown generally as cartridge channel 138 including other aspects of the disclosure. The cartridge channel 138 is substantially similar to cartridge channel 38 (FIG. 3) but includes flexible dimples 140 on an outer surface of the cartridge channel 138. The dimples 140 are supported on cantilevered portions 142 of the cartridge channel 138. The dimples 140 define raised surfaces that engage the extension 84 (FIG. 13) supported on the second beam 78 of the clamp member 74 when the drive assembly 70 (FIG. 3) is advanced in the direction of arrow "C" in FIG. 13 to move the tool assembly 16 (FIG. 8) to the clamped position. Engagement between the dimples 140 and the extension 84 increases the force on the cartridge assembly 32 applied by the extension 84 to urge the cartridge assembly 132 (FIG. 12) towards the anvil 30 to the insertion position in which the distal end portion of the staple cartridge 40 engages the distal end portion of the anvil 30 and/or the tool assembly is maintained in the clamped position in which the tissue gap between the cartridge assembly 32 and the anvil 30 at a distal end of the tool assembly 16 does not exceed a predetermined tissue gap "G". The cantilevered portions 142 allow the dimples 140 to flex inwardly in the direction of arrow "D" out of the path of the second beam 78 (FIG. 13) of the clamp member 74. This allows the clamp member 74 to pass over the dimples 140 when the clamp member 74 is advanced to fire staples from the stapling device 10.

Persons skilled in the art will understand that the devices and methods specifically described herein and illustrated in the accompanying drawings are non-limiting exemplary aspects of the disclosure. It is envisioned that the elements and features illustrated or described in connection with one exemplary embodiment may be combined with the elements and features of another without departing from the scope of the present disclosure. As well, one skilled in the art will appreciate further features and advantages of the disclosure based on the above-described aspects of the disclosure. Accordingly, the disclosure is not to be limited by what has been particularly shown and described, except as indicated by the appended claims.

What is claimed is:

1. A stapling device comprising:
an elongate body having a proximal end portion and a distal end portion;
a tool assembly supported on the distal end portion of the elongate body, the tool assembly including an anvil and a cartridge assembly, the cartridge assembly being movable in relation to the anvil from between an open position to a clamped position in which the cartridge assembly and the anvil define a predetermined tissue gap, the cartridge assembly including a cartridge channel and a staple cartridge having a distal end portion, the cartridge channel including an outer surface defining a ramp; and
a drive assembly including a drive beam and a clamp member, the drive beam having a distal end portion, the clamp member supported on the distal end portion of the drive beam and including a first beam, a second beam, and a vertical strut interconnecting the first beam and the second beam, the vertical strut having a distal end, the drive assembly movable between a retracted position and a partially advanced position to move the second beam into the ramp to move the tool assembly from the open position to the clamped position, and movable from the partially advanced position to a fully advanced position to actuate the tool assembly, the first beam engaging the anvil and the second beam engaging the cartridge channel of the cartridge assembly;
wherein the second beam supports a distal extension that extends distally of the first beam, the second beam, and the distal end of the vertical strut, the distal extension engaging the outer surface of the cartridge channel distally of the ramp when the drive assembly is in the partially advanced position to maintain the tool assembly in the clamped position.

2. The stapling device of claim 1, wherein the outer surface of the cartridge channel includes dimples positioned distally of the ramp, the distal extension of the second beam engaging the dimples when the drive assembly is in the partially advanced position.

3. The stapling device of claim 2, wherein the dimples are supported on cantilevered portions of the cartridge channel, the cantilevered portions allowing the flexible dimples to flex out of the path of the second beam when the drive assembly is moved to the advanced position.

4. The stapling device of claim 1, wherein the distal extension extends distally of the first and second beams a distance "X", wherein "X" is from about 0.1 inches and to about 0.25 inches.

5. The stapling device of claim 1, wherein the distal extension has a width and the second beam has a width, the width of the distal extension being smaller than the width of the second beam.

6. The stapling device of claim 1, further including a rotation knob, the rotation knob being rotatably coupled to a handle assembly and supporting the elongate body, wherein rotation of the rotation knob in relation to the handle assembly effects rotation of the elongate body and the tool assembly in relation to the handle assembly.

7. The stapling device of claim 1, further including a handle assembly having a stationary handle and a trigger.

8. A tool assembly comprising:
an anvil;
a cartridge assembly movable in relation to the anvil from an open position to a clamped position in which the cartridge assembly and the anvil define a predetermined maximum tissue gap, the cartridge assembly including a cartridge channel and a staple cartridge having a distal end portion, the cartridge channel including an outer surface defining a ramp; and
a drive assembly including a drive beam and a clamp member, the drive beam having a distal end portion, the clamp member supported on the distal end portion of the drive beam and including a first beam, a second beam, and a vertical strut interconnecting the first beam and the second beam, the vertical strut having a distal end, the drive assembly movable between a retracted position and a partially advanced position to move the tool assembly from the open position to the clamped position, and movable from the partially advanced position to a fully advanced position to actuate the tool assembly, the first beam engaging the anvil and the second beam engaging the outer surface of the cartridge channel of the cartridge assembly;
wherein the second beam includes a distal extension that extends distally of the first beam and the distal end of the vertical strut, the distal extension engaging the outer surface of the cartridge channel distally of the ramp when the drive assembly is in the partially advanced position to maintain the tool assembly in the clamped position.

9. The tool assembly of claim 8, wherein the outer surface of the cartridge channel includes dimples positioned distally of the ramp, the distal extension of the second beam engaging the dimples when the drive assembly is in the partially advanced position.

10. The tool assembly of claim 9, wherein the dimples are supported on cantilevered portions of the cartridge channel, the cantilevered portions allowing the flexible dimples to flex out of the path of the second beam when the drive assembly is moved to the advanced position.

11. The tool assembly of claim 8, wherein the distal extension extends distally of the first and second beams a distance "X", wherein "X" is from about 0.1 inches and to about 0.25 inches.

12. A tool assembly comprising:
- an anvil;
- a cartridge assembly movable in relation to the anvil from between an open position and a clamped position in which the cartridge assembly and the anvil define a predetermined maximum tissue gap, the cartridge assembly including a cartridge channel and a staple cartridge having a distal end portion, the cartridge channel including an outer surface defining a ramp; and
- a drive assembly including a drive beam and a clamp member, the drive beam having a distal end portion, the clamp member supported on the distal end portion of the drive beam and including a first beam, a second beam, and a vertical strut interconnecting the first beam and the second beam, the second beam having a first width, the drive assembly movable between a retracted position and a partially advanced position to move the tool assembly from the open position to the clamped position, and movable from the partially advanced position to a fully advanced position to actuate the tool assembly, the first beam engaging the anvil and the second beam engaging the cartridge channel of the cartridge assembly;
- the second beam including a distal extension that extends distally of the first beam, the distal extension having a second width smaller than the first width of the second beam, the distal extension engaging the outer surface of the cartridge channel distally of the ramp when the drive assembly is in the partially advanced position to maintain the tool assembly in the clamped position, wherein the outer surface of the cartridge channel includes dimples positioned distally of the ramp, the distal extension of the second beam engaging the dimples when the drive assembly is in the partially advanced position.

13. The tool assembly of claim 12, wherein the dimples are supported on cantilevered portions of the cartridge channel, the cantilevered portions allowing the flexible dimples to flex out of the path of the second beam when the drive assembly is moved to the advanced position.

14. The tool assembly of claim 12, wherein the distal extension extends distally of the first and second beams a distance "X", wherein "X" is from about 0.1 inches and to about 0.25 inches.

* * * * *